(12) United States Patent
Sivaraj

(10) Patent No.: US 9,737,761 B1
(45) Date of Patent: Aug. 22, 2017

(54) SYSTEM AND METHOD FOR FITNESS TESTING, TRACKING AND TRAINING

(71) Applicant: Revvo, Inc., Pittsford, NY (US)

(72) Inventor: Govindarajan Sivaraj, Pittsford, NY (US)

(73) Assignee: REVVO, Inc., Pittsford, NY (US)

( * ) Notice: Subject to any disclaimer, the term of this patent is extended or adjusted under 35 U.S.C. 154(b) by 0 days.

(21) Appl. No.: 14/926,436

(22) Filed: Oct. 29, 2015

Related U.S. Application Data

(60) Provisional application No. 62/072,023, filed on Oct. 29, 2014.

(51) Int. Cl.
*A63B 24/00* (2006.01)
*A61B 5/02* (2006.01)

(52) U.S. Cl.
CPC ............ *A63B 24/0087* (2013.01); *A61B 5/02* (2013.01); *A63B 24/0062* (2013.01); *A63B 2230/04* (2013.01); *A63B 2230/045* (2013.01)

(58) Field of Classification Search
CPC ............ A63B 24/0087; A63B 24/0062; A63B 2230/045; A63B 2230/04; A61B 5/02
See application file for complete search history.

(56) References Cited

U.S. PATENT DOCUMENTS

| | | | | |
|---|---|---|---|---|
| 5,857,939 A * | 1/1999 | Kaufman | ................ | A63B 24/00 482/1 |
| 7,232,416 B2 * | 6/2007 | Czernicki | .............. | A61B 7/006 482/6 |
| 8,533,001 B2 * | 9/2013 | Skiba | ................. | A63B 24/0006 482/8 |
| 8,840,569 B2 * | 9/2014 | Flaction | ............. | G06K 9/00342 340/573.1 |
| 8,990,006 B1 * | 3/2015 | Wallace | ............... | G01C 22/006 701/408 |
| 9,237,868 B2 * | 1/2016 | Seppanen | .............. | A61B 5/222 |
| 9,358,426 B2 * | 6/2016 | Aragones | ........... | G06F 19/3437 |
| 2002/0086774 A1 * | 7/2002 | Warner | .............. | A63B 24/0021 482/8 |
| 2003/0163287 A1 * | 8/2003 | Vock | .................... | A43B 3/0005 702/187 |
| 2007/0135264 A1 * | 6/2007 | Rosenberg | ......... | A63B 24/0006 482/8 |
| 2007/0173377 A1 * | 7/2007 | Jamsen | ................ | A61B 5/1123 482/8 |
| 2007/0232453 A1 * | 10/2007 | Hanoun | ............... | A63B 21/225 482/7 |
| 2007/0232454 A1 * | 10/2007 | Kagan | .................... | A61B 5/024 482/8 |
| 2008/0109257 A1 * | 5/2008 | Albrecht | ............... | G06F 19/345 705/2 |
| 2008/0124752 A1 * | 5/2008 | Ryals | ................... | C12Q 1/6876 435/29 |
| 2009/0062627 A1 * | 3/2009 | Younger | ............ | A63B 24/0003 600/301 |

(Continued)

*Primary Examiner* — Sundhara Ganesan
(74) *Attorney, Agent, or Firm* — Cesari and McKenna, LLP

(57) ABSTRACT

A system and method for adaptive fitness testing is provided. A fitness testing application manages fitness tests on a fitness testing apparatus by collecting physiological data and calculating various performance metrics. The fitness testing application automatically reconfigures fitness tests to adopt to a user's improving fitness level.

19 Claims, 21 Drawing Sheets

(56) References Cited

U.S. PATENT DOCUMENTS

| | | | | |
|---|---|---|---|---|
| 2009/0210078 | A1* | 8/2009 | Crowley | G06Q 30/02 700/91 |
| 2010/0259407 | A1* | 10/2010 | Tilvis | A63B 24/0062 340/686.6 |
| 2011/0004126 | A1* | 1/2011 | Einav | G06F 19/3481 600/595 |
| 2011/0152045 | A1* | 6/2011 | Horne | A63B 24/0062 482/131 |
| 2011/0281249 | A1* | 11/2011 | Gammell | A63B 24/0075 434/247 |
| 2012/0184823 | A1* | 7/2012 | Chen | A61B 5/0205 600/301 |
| 2012/0220429 | A1* | 8/2012 | Yoshida | A63B 71/0686 482/8 |
| 2012/0232360 | A1* | 9/2012 | Maueler | A61B 5/0205 600/301 |
| 2013/0072353 | A1* | 3/2013 | Alessandri | A63B 21/062 482/8 |
| 2013/0079907 | A1* | 3/2013 | Homsi | A63B 24/00 700/91 |
| 2013/0171599 | A1* | 7/2013 | Bleich | A61B 5/0456 434/247 |
| 2013/0174073 | A1* | 7/2013 | Ash | G06F 3/048 715/771 |
| 2013/0190903 | A1* | 7/2013 | Balakrishnan | A61B 5/7246 700/91 |
| 2013/0325498 | A1* | 12/2013 | Muza, Jr. | G06F 19/3437 705/2 |
| 2013/0338802 | A1* | 12/2013 | Winsper | G06F 19/3481 700/92 |
| 2015/0164378 | A1* | 6/2015 | Baker | A61B 5/1036 600/473 |
| 2016/0055758 | A1* | 2/2016 | Francis | G06F 19/3431 434/236 |

* cited by examiner

FIG. 7

|  | 1205 | 1210 | 1215 | 1220 |
|---|---|---|---|---|
|  | Power (Watts) | METs | VO2 | Road Biking Speed |
| Anaerobic | 275 w | 15.9 | 56 | 16.6mph |
| | 170 w | 9.9 | 35 | 12.5mph |

FIG. 12

| Age | 23 |
|---|---|
| Height | 72 |
| Weight | 160 |
| BMI | 21.7 |

| Interval | Watts | HR | EPP | VO2 | METs | 30-sec Recovery | | implied w/ efficiency | hr approach | |
|---|---|---|---|---|---|---|---|---|---|---|
| #1 | 72 | 119 | 119 | | | 6 | | 68 | 0.95 | |
| #2 | 102 | 123 | 163 | | | 14 | 0.11 | 90 | 0.89 | |
| #3 | 131 | 133 | 194 | | | 11 | 0.08 | 120 | 0.92 | |
| #4 | 159 | 141 | 222 | | | 15 | 0.11 | 142 | 0.89 | |
| #5 | 195 | 153 | 251 | | | 20 | 0.13 | 170 | 0.87 | |
| #6 | 224 | 162 | 272 | 34 | 9.8 | 8 | 0.05 | 213 | 0.95 | Anaerobic Threshold |
| #7 | 260 | 170 | 301 | | | 15 | 0.09 | 237 | 0.91 | |
| #8 | 255 | 176 | 285 | | | 7 | 0.04 | 245 | 0.96 | |
| #8 | 284 | 179 | 313 | | | | | 284 | 1.00 | |
| #9 | 313 | 183 | 337 | 51 | 14.7 | | | 313 | 1.00 | |
| | | | | | | | | average | 0.92 | |
| | | | | | | | | max | 0.96 | |
| | | | | | | | | min | 0.87 | |
| | | | | | | | | range | 0.09 | |

FIG. 13

SYSTEM AND METHOD FOR FITNESS TESTING, TRACKING AND TRAINING

CROSS-REFERENCE TO RELATED APPLICATIONS

The present application claims the benefit of U.S. Provisional Patent Application Ser. No. 62/072,023, which was filed on Oct. 29, 2014, by Govindarajan Sivaraj for a System and Method for Fitness Testing, Tracking and Training and is hereby incorporated by reference.

FIELD OF THE INVENTION

The present disclosure is directed to fitness testing and, more particularly to adaptive and personalized fitness testing.

BACKGROUND OF THE INVENTION

VO2Max (cardio-respiratory fitness) is well established as one of the best indicators of fitness and health. Elite athletes typically have VO2Max levels that are twice as high as an average person. VO2Max also correlates with a number of health conditions such as, diabetes, hypertension and is considered the single best predictor of cardiovascular risk and all-cause mortality. However, prior art techniques for measuring and monitoring VO2Max, have a number of disadvantages. Notably, prior art methods for measuring fitness metrics are expensive and cumbersome to administer. For example, the requirements of breathing through an oxygen mask complicates test administration. Further, prior art techniques require substantial labor intensive work to perform a correct test. As can be appreciated by one skilled in the art, those with low levels of fitness could benefit most greatly from improvements in their fitness level; however, prior art techniques do not accurately obtain fitness information from those with extremely low levels of fitness. Further, even for those who have a level of fitness where current techniques can obtain meaningful results, the person also needs guidance as to how best to exercise in a way to improve the fitness metrics and concomitantly, their own health. Such guidance is not obvious to users, including highly trained exercise physiologist, without accurate measurements and analysis of fitness metrics. Further, as is well known, without constant adaptation of one's exercise regimen, a person may plateau in their improvements, which may lead to frustration and/or abandonment of a fitness regimen. A further noted problem is that there is a lack of good blood pressure and blood glucose monitoring that is available for home use. Additionally, such use measurement systems only assess the severity of symptoms and do not tackle the root cause behind blood glucose and/or blood pressure issues.

SUMMARY OF THE INVENTION

The disadvantages of the prior art are overcome by a system and method for fitness testing described herein. Illustratively, a user's fitness parameters are estimated for such person as VO2Max, anaerobic threshold and heart rate recovery via a fitness test adaptable to users of any level of fitness. A fitness testing application, in conjunction with a testing apparatus, develops a personalized exercise plan for the user and then tracks ongoing improvements in fitness parameters as a user participates in the exercise program. Notably, the fitness testing system does not require repeated/daily fitness tests.

Illustratively, a fitness testing application implementing illustrative embodiments of the present invention, executes on a fitness testing computer that is operatively interconnected with a fitness testing apparatus as well as a heart rate monitor. The fitness testing apparatus is illustratively an exercise bicycle configured to operate with a motorized trainer that may selectively vary the resistance. The trainer is operated under the control of the fitness testing application. The fitness testing application leads a user through a fitness regimen and collects data from the user that is stored for analysis to adapt a training regimen to the user's fitness improvements.

BRIEF DESCRIPTION OF THE DRAWINGS

The above and further advantages of the present invention may be shown in relation to the following accompanying drawings in which like reference numerals indicate the same or functionally similar elements:

FIG. 7 is an exemplary screenshot illustrating a fitness test plan window in accordance with an illustrative embodiment of the present invention;

FIG. 12 is an exemplary screenshot illustrating an anaerobic threshold window in accordance with an illustrative embodiment of the present invention;

FIG. 13 is an exemplary screenshot illustrating an example calculations window in accordance with an illustrative embodiment of the present invention;

DETAILED DESCRIPTION OF AN ILLUSTRATIVE EMBODIMENT

Overview

Figure 1:
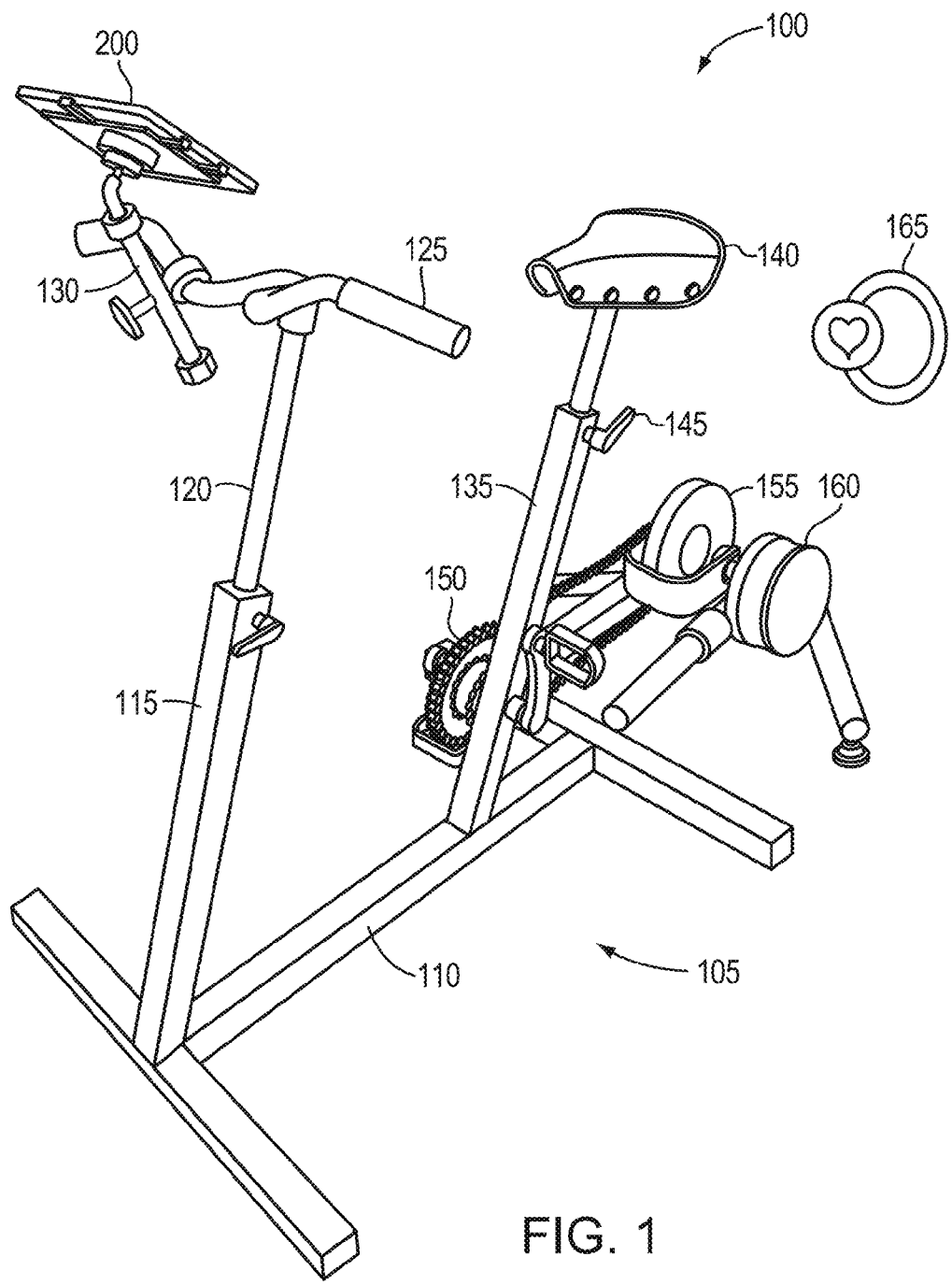
FIG. 1 is a schematic diagram of an exemplary fitness testing environment in accordance with an illustrative embodiment of the present invention.

It is well known that exercise, whether exclusively or in combination with other behavioral modifications e.g., diet changes and smoking cessation, can be effective in primary and secondary prevention of many health conditions such as diabetes, hypertension and/or heart disease. It has also become apparent that increasing physical fitness is more effective at improving health and mitigating illness compared to general increases in physical activity. For example, cardio-respiratory fitness (VO2Max) has been shown to be the number one predictor of morbidity and mortality related to cardiovascular disease. Further, the anaerobic threshold has been shown to closely correlate with insulin sensitivity. Finally, heart rate recovery has been shown to closely correlate with fasting plasma glucose as well as blood pressure. Exercising at or just above the anaerobic threshold has also been recognized as the optimal intensity for improving insulin sensitivity and hypertension.

A first noted problem is that current methods to measure these metrics suffer from a number of shortcomings and are not very applicable for people with lower levels of fitness. As will be appreciated by those skilled in the art, those with lower levels of fitness would most benefit from such measurements. The current best practice approach to measuring cardio-respiratory fitness is a maximal test using the 'metabolic cart' where respiratory ratio ($VO_2$, $VCO_2$) of the user is measured while the test participant increases their exercise intensity progressively until the participant has reached their maximum capacity or their $VO_2$ levels plateau, whichever is earlier. 'Sub-maximal' exercise testing protocols, e.g., the protocol described in Bruce, are also commonly used where the user's heart rate (HR) is measured alongside their $VO_2$ results as they progressively increase exercise intensity. Test participants typically end their session when they reach close to age specific heart rate (HR) max or fatigue and VO2Max is estimated by projecting HR/$VO_2$ ratio at the end of the test to Max HR for that user. In some cases work rate (watts) is measured instead of $VO_2$ and VO2Max inferred from Estimated Peak Watts (EPW) based on standard metabolic equations, e.g., American College of Sports Medicine (ACSM) equations. Measuring the anaerobic threshold requires analyzes of the respiratory gases—specifically the $VO_2/VCO_2$ ratio. The point of significant deviation from the linear trend is marked as the anaerobic threshold.

The above methods suffer from a number of shortcomings namely, (i) measuring respiratory gases requires expensive lab equipment and trained staff to administer the test, (ii) current tests take significant time—typically 10-12 minutes in set-up time, up to 30 minutes in calibration, followed by the actual test itself, (iii) many tests follow a standardized protocol with uniform increments in intensity and do not reflect the varying levels of fitness in the general population, (iv) patients with low levels of fitness (such as those suffering from diabetes, obesity or cardiovascular disease) typically reach fatigue very early in the test process—well before they get close to maximum heart rate, significantly reducing the precision of CRF through such protocols, (v) patients have to undergo breathing into an oxygen mask while running or cycling at high intensity, which is not pleasant and dissuades many patients from taking the test, (vi) test administrators cannot verbally communicate with the test taker, thereby needing to rely on hand signals, and (vi) importantly none of these approaches are designed to track changes in these metrics as users start on a exercise program, users therefore have to undergo repeat tests to measure their progress/quantify improvement.

As a result even well equipped medical centers typically end up using a simple 6 minute walk test to establish baseline fitness for patients with diabetes or cardiovascular condition. Such walking tests are easy to administer and considered relatively safe for the vast majority of patients and can be repeated whenever appropriate. The distance covered in 6 minutes is typically used as the benchmark. However the test suffers from a number of defects—it is very approximate, fails to estimate CRF or the anaerobic threshold, test-re-test reliability is often poor and it requires a sizeable/obstacle free space to administer.

A second noted problem is that knowing a patient's fitness and anaerobic threshold is not sufficient—people also need guidance on how best to workout in a way that improves these metrics and as a result their health. This is not obvious even to an exercise physiologist without accurate measurements and analysis, let alone a lay user. Further, there is a need to constantly adapt the workout to training induced changes in the user's physiology in order to continue to gain benefits from a program like this, otherwise users tend to see their progress plateau.

Today's exercise technologies (e.g., exercise bikes, treadmills, elliptical machines) typically expect the user to know what to do and do not usually provide guidance to the user on the precise workout they should adopt in order to maximize improvements in their fitness or health. In addition they do not have the necessary analytics in place to track or display these user specific improvements in cardio-respiratory fitness, anaerobic threshold or heart rate recovery and to suggest changes in their workout plan based on changes in these parameters. As a result (i) users do not workout at the optimal level, (ii) they do not see results of sufficient magnitude, (iii) initial gains are not sustained—they plateau, and (iv) users give up because they don't see results and therefore drop out of exercise programs. This results in an epidemic of lifestyle diseases.

A third problem is that home measurement of blood pressure and/or blood glucose (BG) monitoring is widely available and is used to judge if the user's health is improving, declining or under control. However these measurements are prone to a number of issues/errors: (i) they require user training to collect accurate information, (ii) the accuracy is often low—e.g. BG monitoring is FDA regulated to provide 95% confidence of a +/−20% interval versus gold standard, (iii) are affected by a large number of factors (e.g.

time of the day, crossing your leg, etc. are all factors that affect BP measurement) that makes interpreting these results a rather subjective exercise, and (iv) blood pressure and blood glucose medications have a transient effect on these metrics, temporarily reducing these without necessarily changing the underlying problem. Importantly these measurements only assess the severity of the symptoms and not the root cause and therefore encourage treatment methods that address symptoms rather than correct the underlying problem.

Illustrative embodiments of the present invention create a novel approach to estimating fitness parameters for an individual, such as the VO2Max, anaerobic threshold and the heart rate recovery via a novel fitness test that is suitable for individuals at any level of fitness. Embodiments of the present invention then use the information from the fitness test to devise a personalized exercise plan for the user and tracks ongoing improvements in fitness parameters as the user participates in the exercise program, while avoiding having to subject the user to repeated/daily fitness tests. The invention intelligently adapts the exercise plan when fitness parameters and/or exercise capacity sufficiently change. In addition it anticipates changes in the user's heart rate during the exercise session and adapts the exercise intensity accordingly to prevent the user's heart rate from exceeding safe limits.

By maintaining the user's work rate at or above the user's critical thresholds such as the aerobic threshold or lactate/anaerobic threshold or OBLA or VO2Max on a regular basis, embodiments of the present invention are able to achieve a number of previously unachievable outcomes, namely (i) improve, even normalize insulin sensitivity and blood glucose control, (ii) improve, even normalize blood pressure (iii) significantly and continuously improve VO2Max, even for individuals with lower response to exercise, (iv) raise the anaerobic threshold, (v) improve heart rate recovery, (vi) reduce the risk of cardiovascular morbidity and/or mortality, (vii) minimize the probability of a hypoglycemic episode for users with diabetes, (vii) permits patients with diabetes, hypertension, heart disease and other health conditions to safely participate in a primary, secondary or tertiary prevention program, and (viii) increase resting energy expenditure leading to sustained weight loss In accordance with an illustrative embodiment, the present invention comprises of (i) a technique to estimate the user's cardio-respiratory fitness (expressed as $VO_2$ or in METs), anaerobic threshold (AT, expressed as % $VO_2$ or in METs) and their heart rate recovery (expressed as a % or in absolute beats per minute) that works for users across a wide range of fitness levels, is non-invasive and can be safely conducted at home (or other locations) without the physical presence of trained personnel (ii) a technique to estimate an displaying ongoing changes in these above metrics basis the exercise data obtained during each session, (iii) a exercise training protocol (adaptive interval training) that makes it possible for users across a wide range of fitness levels to workout just above their lactate/anaerobic threshold or even their VO2Max and therefore benefit from the resulting rapid improvement in their health and fitness, (iv) a software interface that reads information related to the heart rate of the user (measured in bpm or equivalent) alongside their energy expenditure (measured in watts or equivalent) and which modifies the desired energy expenditure basis the heart rate patterns—both by indicating to the user as well as directly altering the exercise equipment (e.g. by changing the resistance on the exercise bike), (v) a software interface that makes it safe for users with diabetes or cardiovascular disease to exercise by keeping blood pressure and blood glucose levels during the exercise program within safe limits by manipulating the duration and intensity of each interval and the duration of the recovery period, and (vi) an exercise training protocol that alternates workout intensity just above and below the anaerobic threshold to minimize the incidence of exercise related hypoglycemic events for type 1 diabetes patients Underlying all the embodiments described herein is a software application that is connected with and collects information on both the user's energy expenditure (e.g. power in watts) and their heart rate. Information on heart rate could be obtained via commercially available heart rate monitors—ECG monitors, chest worn heart rate straps or hand worn heart rate monitors, pulse oximeters etc. Information on the user's energy expenditure could be estimated using for e.g. the accelerometer or directly measured via the exercise equipment (e.g. exercise bike or treadmill).

Fitness Test Environment

FIG. 1 is a schematic diagram of an exemplary fitness testing environment 100 that may be utilized in accordance with an illustrative embodiment of the present invention. Illustratively, the environment 100 includes a fitness apparatus 105 that may, in accordance with an illustrative embodiment of the present invention, be implemented as a stationary exercise bicycle modified in accordance with the teachings of the present disclosure. It should be noted that while the illustrative embodiments are written in terms of using a stationary bicycle as the fitness apparatus 105, alternative embodiments may utilize any cardiovascular training machine, e.g., a treadmill, rowing machine, etc. As such, the description of a stationary bicycle as the fitness apparatus 105 should be taken as exemplary only.

The exercise apparatus 105 illustratively comprises a base 110 that is connected with a front frame portion 115 and a rear frame portion 135. The front frame portion 115 illustratively includes a telescopic handle bar support 120 that terminates with a set of handlebars 125. A computer mount 130 may be connected to the handlebars 125 or handlebar support 120. The computer mount 130 illustratively includes a mounting bracket and support for a fitness testing computer 200, described further below in reference to FIG. 2. Generally, in accordance with an illustrative embodiment, the fitness testing computer comprises a tablet computer that is operatively interconnected the trainer 160 and heart rate monitor 165, described further below. However, it should be noted that in alternative embodiments of the present invention, the fitness testing computer 200 may be another form of computing device. As such, the description of a tablet computer should be taken as exemplary only.

The rear frame 135 illustratively supports a saddle 140 that may be height adjusted via adjustment lever 145. Also connected to the rear frame 135 is a set of pedals 150 that operatively interconnected with a rear wheel/flywheel 155 that is further operatively interconnected with a bike trainer 160. Illustratively, the bike trainer 160 provide selectable resistance to the user of the exercise apparatus 105. In accordance with an illustrative embodiment of the present invention, the trainer 160 communicates with the fitness testing computer 200 via a wireless link, such as a Bluetooth connection. However, it should be noted that in alternative embodiments of the present invention, the trainer 160 may communicate with the testing computer via other techniques including, for example, wired communication techniques. As such, the description of trainer 160 being in communication via Bluetooth to the fitness testing computer 200 should be taken as exemplary only.

In accordance with an illustrative embodiment of the present invention, a user (not shown) wears a heart rate monitor 165 during testing. The heart rate monitor 165 may comprise any of a number of form factors, including for example, a wrist worn heart monitor, chest mounted heart monitor, etc. Illustratively, the heart rate monitor is able to communicate with the fitness testing computer 200. Such communications may be via, wired communications or via wireless communications by, for example, a Bluetooth wireless link. In accordance with an illustrative embodiment of the present invention, the heart rate monitor may have a device identifier (Device ID) that is accessible by the fitness testing computer 200. For example, the heart rate monitor 165 may broadcast its Device ID to the fitness testing computer, etc.

Illustratively, in operation, a user is led through a fitness test or training regiment that is managed by the fitness testing computer. Generally, the fitness testing computer 200 provide indications of length of time to exercise to a user as well as manages resistance levels provided by the trainer 160. During a fitness test and resting intervals, the heart rate monitor 165 provides heart rate information to the fitness testing computer for use in tracking and calculating performance metrics, as described further below.

Figure 2:
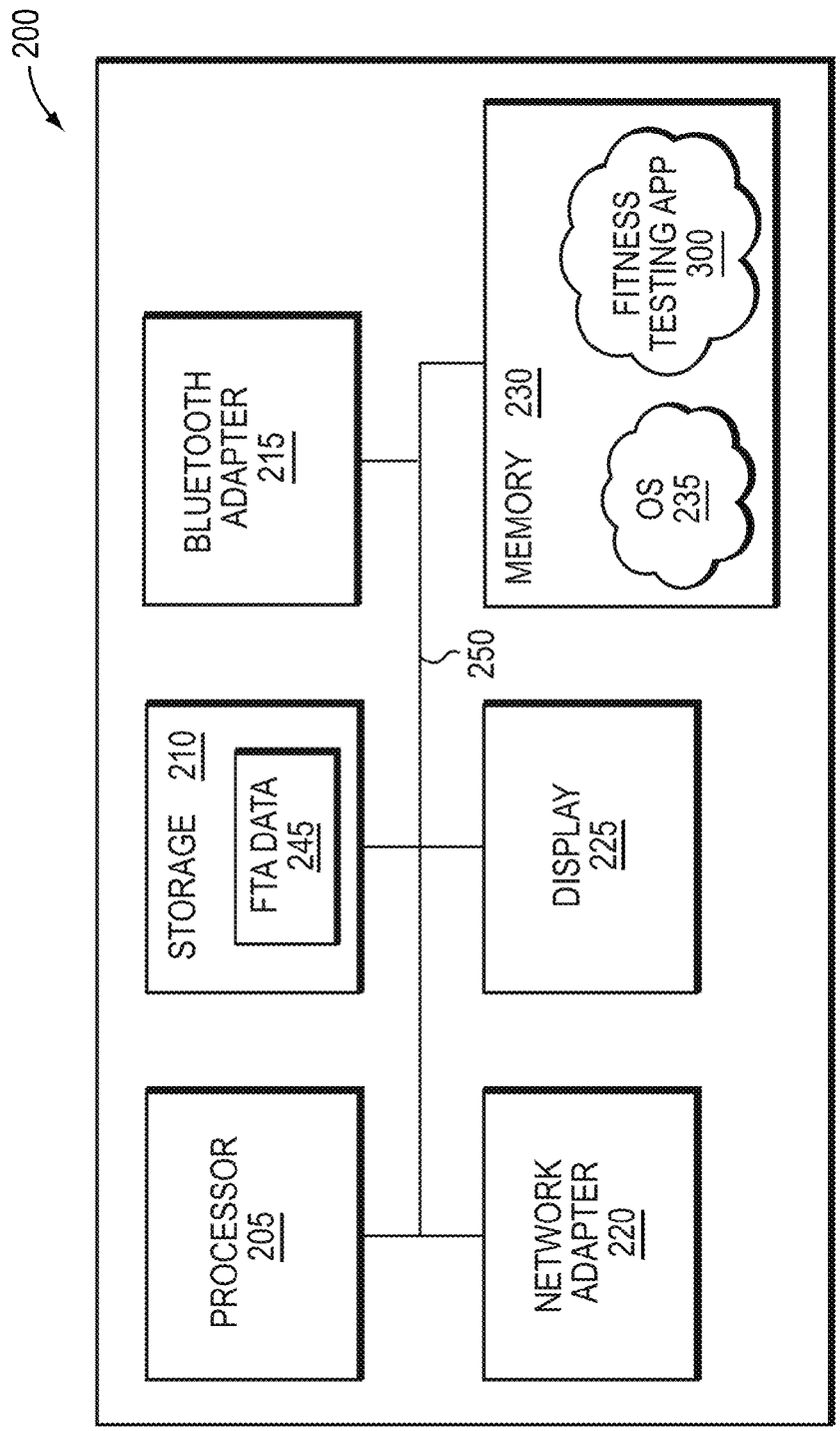
FIG. 2 is a schematic block diagram of an exemplary fitness testing computer in accordance with an illustrative embodiment of the present invention.

FIG. 2 is a schematic block diagram of an exemplary fitness testing computer 200 in accordance with an illustrative embodiment of the present invention. The fitness testing computer 200 may comprise any device capable of executing applications. Illustratively, the fitness testing computer 200 may comprise a tablet computer, such as an iPad tablet available from Apple, Inc. It should be noted that other types of tablets or differing computing devices may be utilized in alternative embodiments of the present invention. As such, the description of a tablet computer being utilized as the fitness testing computer 200 should be taken as exemplary only.

The fitness testing computer 200 illustratively comprises a processor 205, storage 210, Bluetooth adapter 215, network adapter 220, display 225 and memory 230 operatively interconnected by a system bus 250. The Bluetooth adapter 215 and network adapter 220 contain the mechanical, electrical, and signaling circuitry for communicating data over networks. The adapters 215, 220 are illustratively configured to transmit and/or receive data using a variety of different vacation protocols including, inter alia, TCP/IP, UDP, ATM, SONET, HTTP, wireless protocols, frame relay, Ethernet, fiber distributed data interface (FDDI), etc. It should further be noted that while the Bluetooth adapter 215 is shown as a separate component from the network adapter 220, in alternative embodiments, a single adapter may provide both network, such as Wi-Fi, and Bluetooth adapter services. As such, the description of these adapters being separate devices should be taken as exemplary only.

The memory 230 comprises a plurality of locations that are addressable by the processors 205 and adapters 215, 220 for storing software programs and data structures associated with the embodiments described herein. The processor 205 may comprise necessary elements or logic adapted to execute the software programs and manipulate the data structures. An operating system 235, portions of which are typically resident in memory 230 and executed by the processor 205, functionally organizes the fitness testing computer 200 by, inter alia, invoking software processes and/or services or other applications executing thereon. A fitness testing application 300, described further below in reference to FIG. 3, implements, in conjunction with the fitness testing apparatus 105, the various embodiments of the present invention.

Storage 210 may illustratively comprise long term or nonvolatile storage. Fitness testing application data 245 may be stored in storage 210 to enable recovery of the data following crashes, reboots, etc. Storage 210 may comprise any form of persistent storage, e.g., Flash RAM, hard disk drive, non-volatile RAM, etc.

Display 225 is illustratively a touch screen providing input/output functionality. However, it should be noted that in alternative embodiments, display 225 may comprise a non-touch screen display. In such alternative embodiments, suitable input devices (not shown) would be utilized for user input to the fitness testing device.

Figure 3:
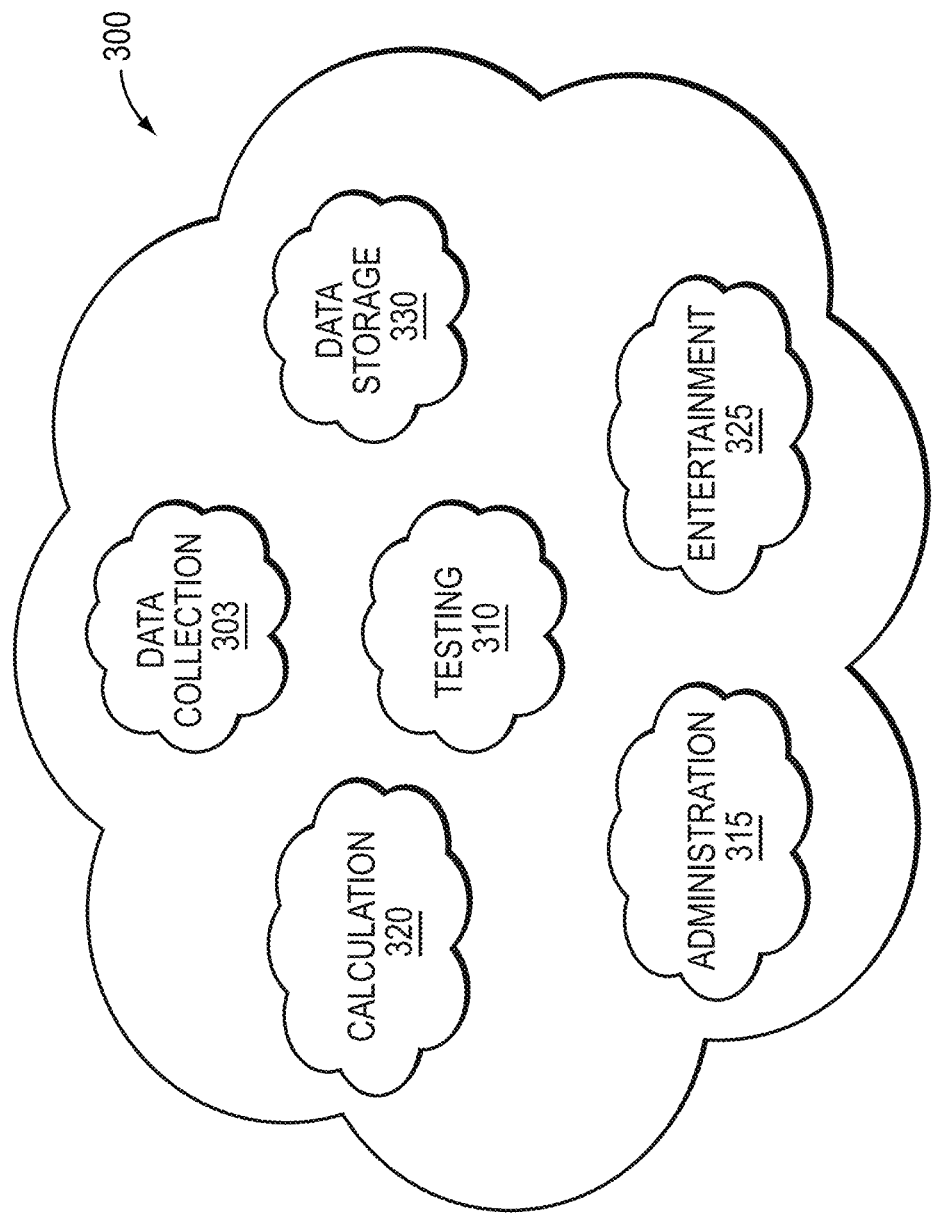
FIG. 3 is a schematic diagram of an exemplary fitness testing application in accordance with an illustrative embodiment of the present invention.

FIG. 3 is a schematic diagram of an exemplary fitness testing application 300 in accordance with an illustrative embodiment of the present invention. Illustratively, the application 300 comprises a data collection module 305, a testing module 310, an administration module 315, a calculation module 320, and entertainment module 325 and a data storage module 330. The data collection module 305 manages the collection of data from bike trainer 160 and/or the heart rate monitor 165. In alternative embodiments, the data collection module 305 may also collect data from other physiological testing apparatus that is utilized with a user of the fitness testing apparatus. The testing module 310 illustratively implements the appropriate fitness tests as configured by an administrator, as described further below. These tests may be implemented by, for example, displaying certain goals on the display 225 of the fitness testing computer 200 and collecting data, via the data collection module 305, of the user's physiological factors, e.g., heart rate, etc.

The administration module 315 manages the fitness testing application 300 and provides administrative functions, e.g., creation of new users, data management, password protection, etc. The calculation module 320 performs any calculations of physiological metrics from the collected data. The entertainment module 325 provides in-testing entertainment on display 225 of the fitness testing computer 200. For example, the entertainment module 325 may provide video playback and/or music functionality to provide a focus for the user during a fitness test. The data storage module 330 manages storage of data for the fitness testing application. In one exemplary embodiment, the data storage module 330 may store data in storage 210 of the fitness testing computer 200. However, in alternative embodiments of the present invention, the data storage module 330 may store fitness testing application data in a cloud-based storage arrangement (not shown). As such, the description of fitness testing application data being stored in the fitness testing computer should be taken as exemplary only.

It should be noted that the various functionality of the modules 305-330 are for illustrative purposes. In various alternative embodiments of the present invention, the functionality may be configured in differing modules, or spread throughout various applications and/or the operating system 235. As such, the description of the fitness testing application 300, or modules thereof, performing various functions should be taken as exemplary only. Generally, the fitness testing application 300 manages the fitness testing in accordance with various embodiments of the present invention. Fitness testing application may gather data from, e.g., bike trainer 160 and/or heart rate monitor 165 for use in computing fitness metrics. Further, in alternative embodiments, the fitness testing application may gather additional data from other physiological measurement devices (not shown). As such, the description of gathering data from trainer 160 and heart rate monitor 165 should be taken as exemplary only.

It should further be noted that while the present description is written in terms of the fitness testing application 300 executing on a tablet computer, such as fitness testing computer 200, the principles of present invention may be implemented in other forms. For example, the fitness testing application may be implemented as an application, mobile device app, process, thread, embedded software, firmware and/or hardware, etc. As such the description of fitness testing application being an application should be taken as exemplary only.

Figure 4:
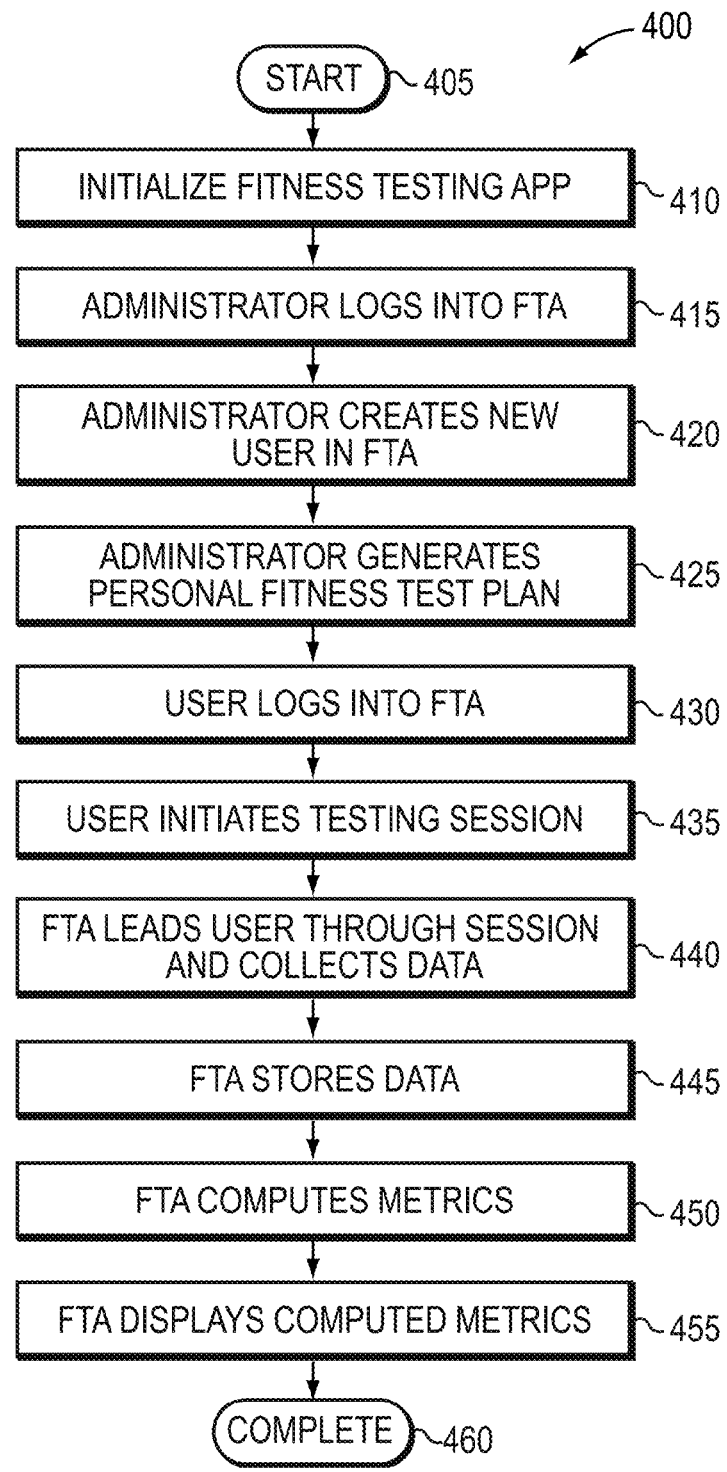
FIG. 4 is a flowchart detailing the steps of a procedure for performing fitness testing in accordance with an illustrative embodiment of the present invention.
Figure 5:
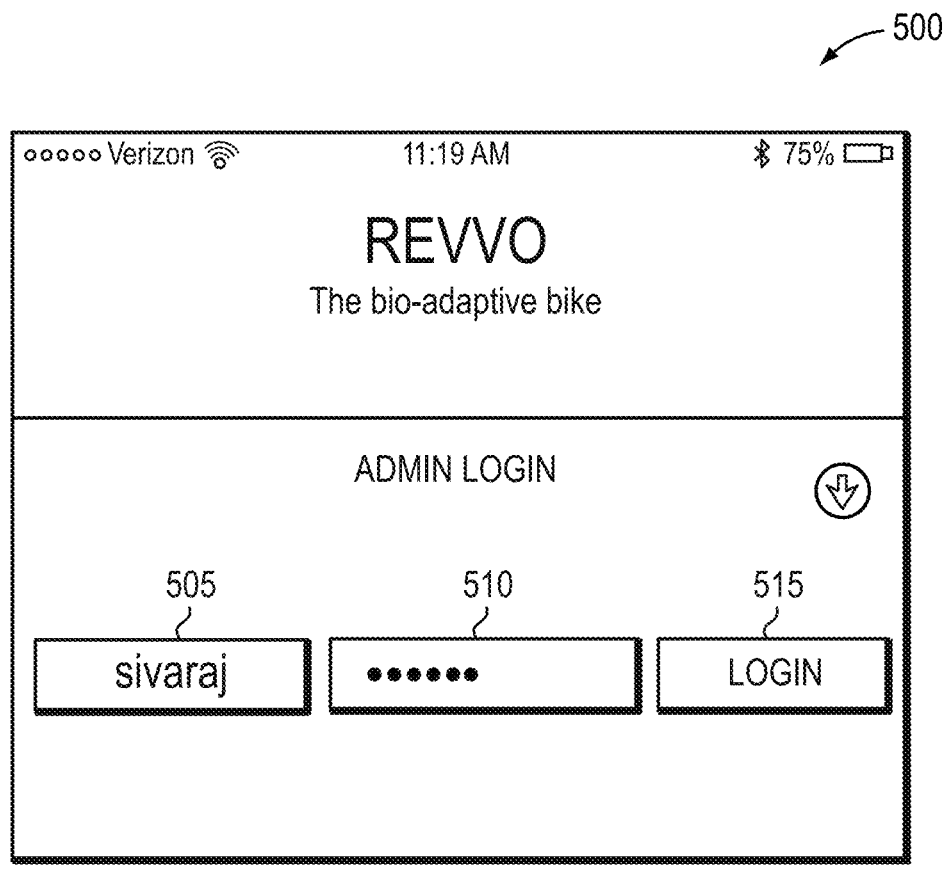
FIG. 5 is a exemplary screenshot illustrating an administrator login window in accordance with an illustrative embodiment of the present invention.

FIG. 4 is a flowchart detailing the steps of the procedure 400 for performing a fitness test in accordance with an illustrative embodiment of the present invention. The procedure 400 begins in step 405 and continues to step 410 where the testing fitness testing application 300 is initialized. Illustratively, this may be performed by an administrator and/or user launching the application on a fitness testing computer 200. For example, when executing on a tablet computer, the fitness testing application 300 may be launched by clicking or double-clicking on a touch screen icon indicative of the fitness testing application 300. Once the fitness testing application has been launched, an administrator then logs into the fitness testing in step 415. FIG. 5 is an exemplary screenshot illustrating an administrator login window 500 in accordance with an illustrative embodiment of the present invention. The login window 500 may be displayed on the display 225 of the fitness testing computer 200 when the application is initialized. In alternative embodiments, there may be a menu option (not shown) to bring a user to the administrative login window 500. The window 500 illustratively comprises a username field 505, password field 510 and a login button 515. The administrator may type his user name in username field 505. Similarly, the administrator may enter his password in password field 510. After entering the username and password, the administrator may then select the login button 515. In response, the fitness testing application 300 may compare the username and password to those stored in its list of permitted administrators. If they match, the administrator is then logged into the fitness testing application 300 and may perform administrative functions.

Figure 6:
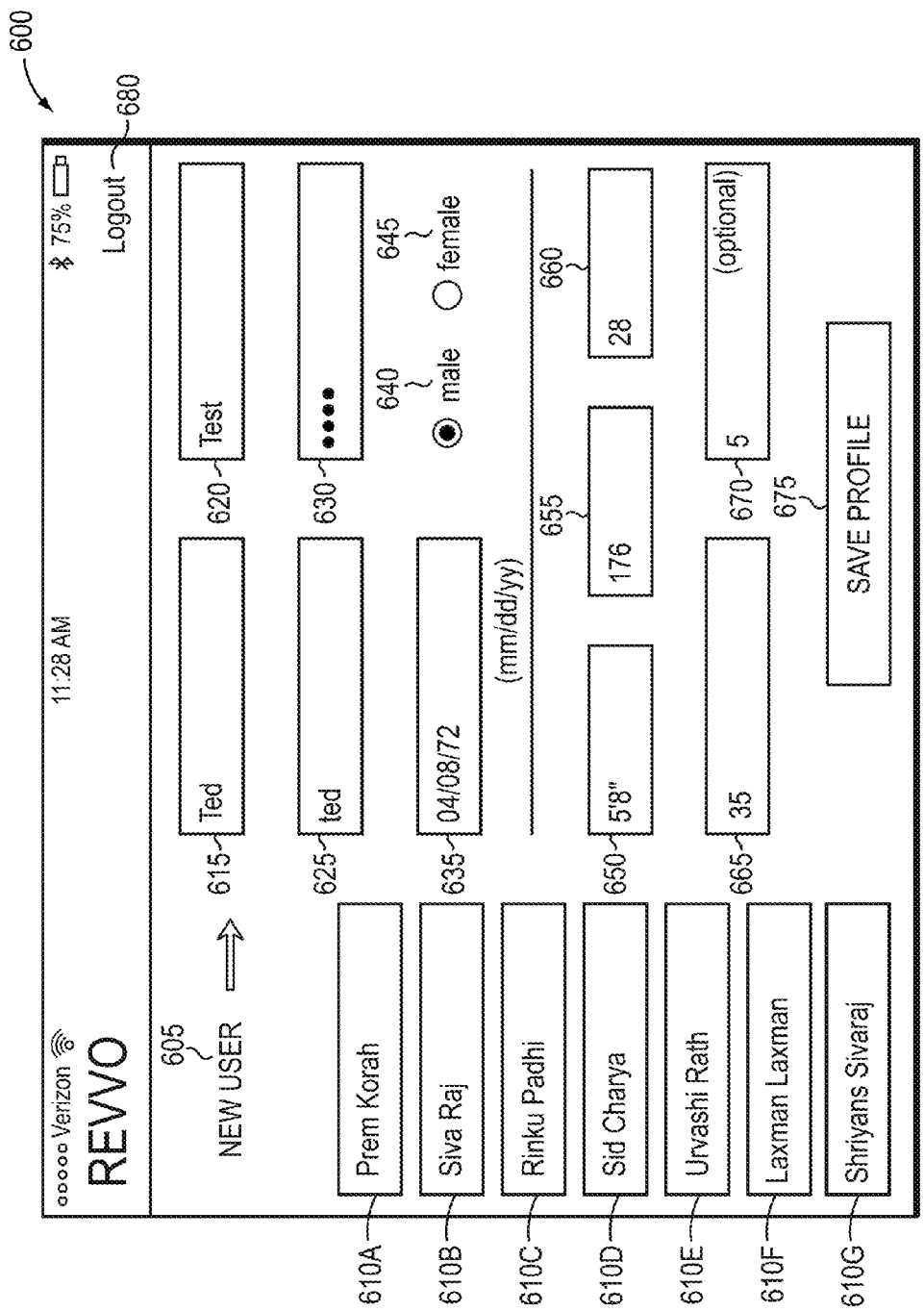
FIG. 6 is an exemplary screenshot illustrating a new user setup window in accordance with an illustrative embodiment of the present invention.

The administer may then create a new user in the fitness testing application in step 420. FIG. 6 is an exemplary screenshot illustrating a new user setup window 600 in accordance with an illustrative embodiment of the present invention. Illustratively, the setup window 600 may be displayed to an administrator for management of users including, for example, the addition of a new user. A new user may be added when, for example, a user is referred to a testing facility for data collection and/or testing. Exemplary window 600 includes a new user button 605, a list of users 610 and additional fields 615-670. A save button 675 is provided that enables an administrator to save the data entered in other fields. Further, a logout button 680 enables the administrator to log out of the fitness testing application. Exemplary fields 615-670 may include, for example, a first name field 615, a last name field 620, a username field 625, password field 630, birthdate field 635, male and female gender selection buttons 640, 645, a height field 650, weight field 655, body fat percentage field 660, waist size field 665 and an activity level field 670. An administrator may illustratively enter the name of a user in the first and last name fields 615, 620. Further, the user may be assigned a username in username field 625. A initial password may be entered in password field 630. The username and password may be utilized by the user to later log into the fitness testing application 300 to perform testing and/or have the fitness testing application track the user's individual fitness performance and progress. The date of birth of field 635 and gender fields 640, 645 enable the administrator to identify the age and gender of the user. Such information may be utilized by the fitness testing application and later calculation of metrics including, for example calculation of a maximum heart rate. As will be appreciated by those skilled in the art, a conventional maximum heart rate may be defined as 220 minus the age in years. The additional physiological fields 650-670 may be utilized to enter information regarding a user for use in calculating the fitness metrics, as described further below. It should be noted that wow window 600 illustrates a particular set of fitness or physiological factors, in alternative embodiments of the present invention additional and/or differing physiological factors may be recorded. As such, the particular factors identified herein and should be taken as exemplary only.

Figure 7:
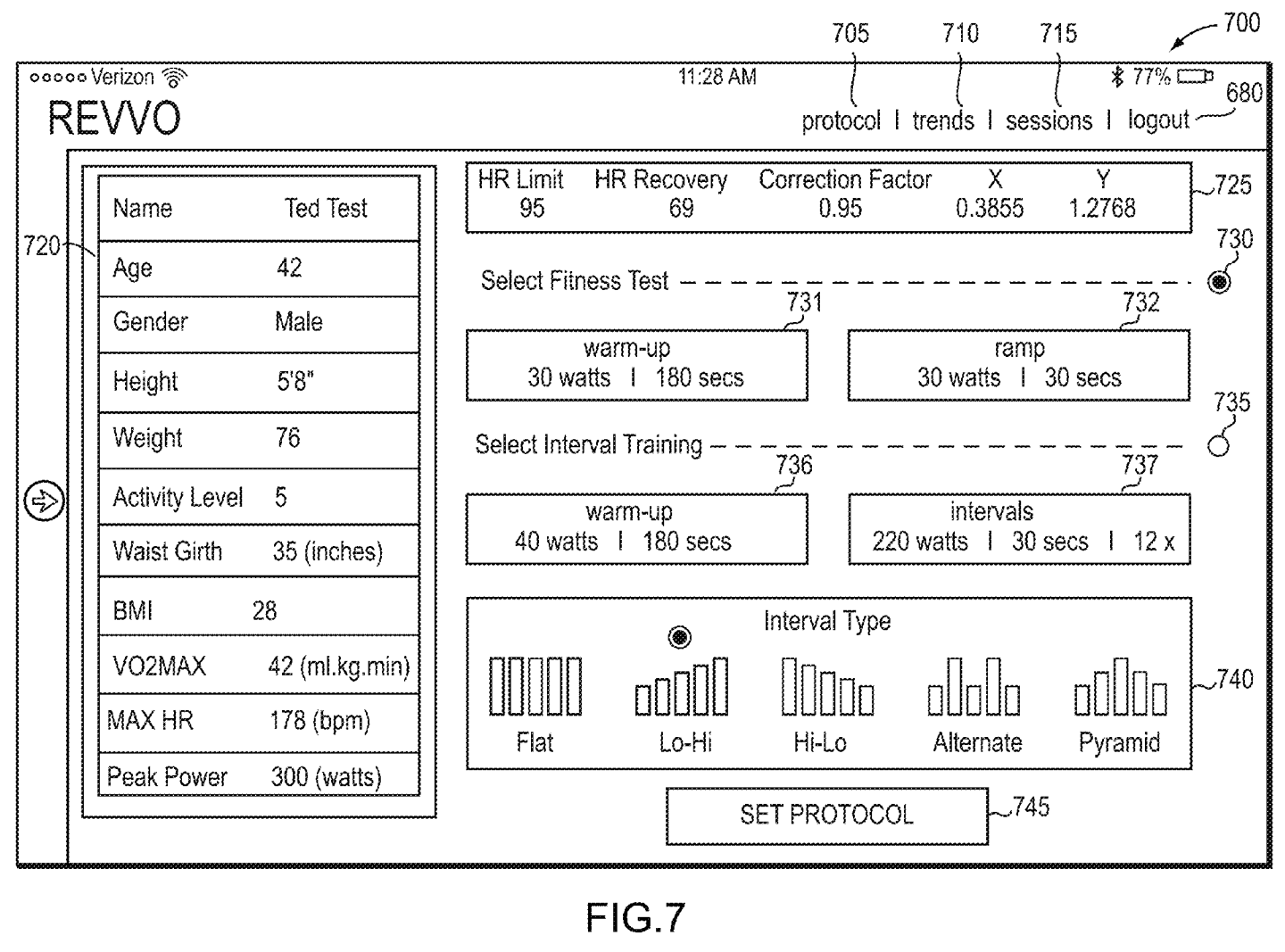
Figure 8:
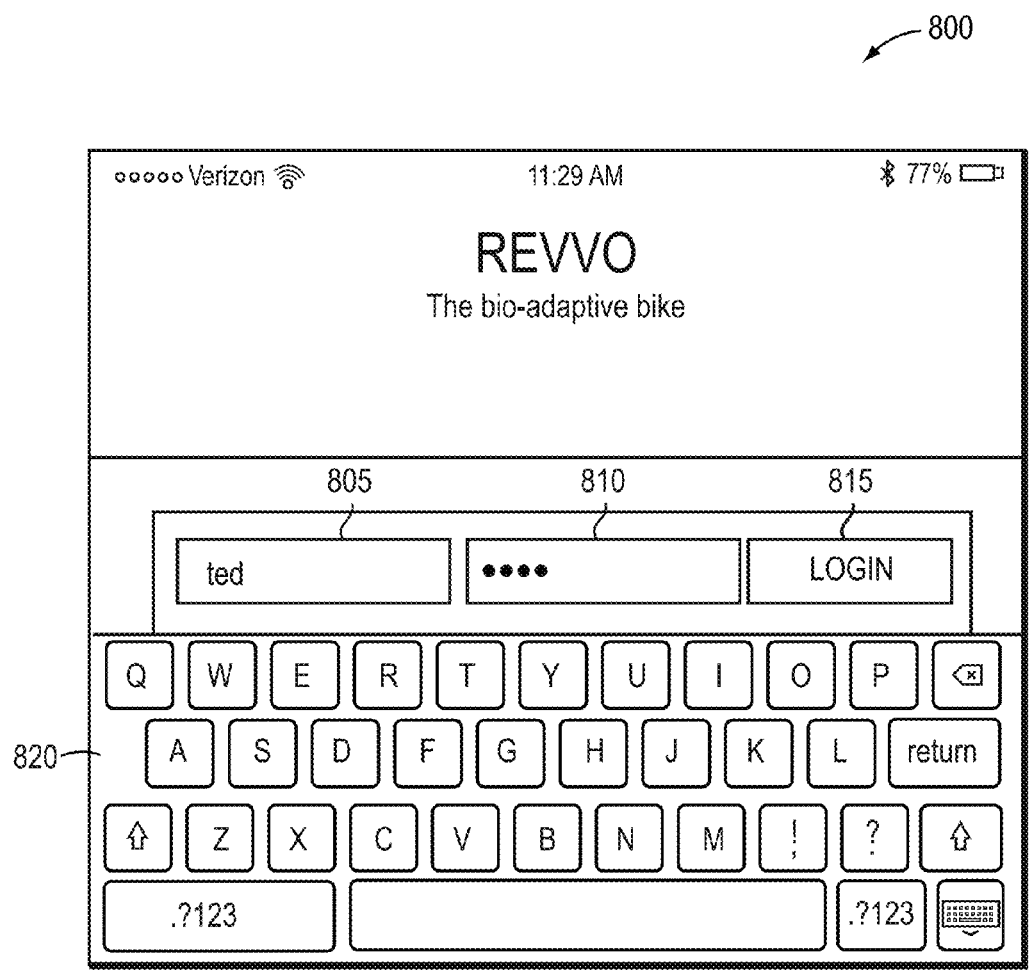
FIG. 8 is an exemplary screenshot illustrating a user login window in accordance with an illustrative embodiment of the present invention.

The administrator may generate a personal fitness test plan for a user in step 425. FIG. 7 is an exemplary screenshot illustrating a fitness test plan window 700 in accordance with an illustrative embodiment of the present invention. The window 700 illustratively comprises a protocol tab 705, a friends tab 710, a sessions tab 715 and a logout button 680. The window 700 also includes a user field 720, physiological factors field 725, fitness test selection button 730, work interval training buttons 735 as well as an interval type selection field 740. The window 700 also includes exemplary fields defining At some later point in time a user may then log into the fitness testing app in step 430. It should be noted that in alternative embodiments, an administrator may not need to create a user account, but such account creation may be accessible to users. As such, the preceding description should be taken to cover those embodiments where an administrator is not required for account creation, etc. FIG. 8 is an exemplary screenshot illustrating a user login window 800 in accordance with an illustrative embodiment of the present invention. The window 800 illustratively includes username field 805, password field 810, login button 815 and an on-screen keyboard 820. As noted above, the fitness testing application 300 illustratively executes on a touchscreen enabled device 200. In such embodiments, the on screen keyboard 820 is utilized to enable users to enter their username and password. For example, a user may enter his username in the username field 805, his password in password field 810 before selecting the login button 815. It should be noted that in accordance with alternative embodiments of the present invention, users may log into the fitness testing application using other techniques. For example, if the fitness testing application 300 is executing on a fitness testing computer 200 that includes biometric security, such as a fingerprint scanner (not shown), a user may login by providing biometric information. In an alternative embodiment, the fitness testing computer may recognize the particular Device ID of a heart rate monitor and log the user in based on the presence of the heart rate monitor 165. In an alternative embodiment, the fitness testing computer may monitor received heart rate rhythms from the heart rate monitor 165 and log a user in based on recognizing the idiosyncrasies of the user's heart rhythm. As such, the description of a user logging into the fitness testing application 300 by entering a username and password should be taken as exemplary only.

After a user has logged into the fitness testing application, the user may initiate a testing session in step 435. Illustratively, the fitness testing application 300 will began a pretty defined testing or exercise session based on the physiological factors entered by the administrator as well as determined from stored data from previous fitness sessions. Illustratively, sessions comprise intervals of exercise with intervals of rest. The exemplary testing sessions. A further description of exemplary testing and training sessions is described further below.

Figure 9:
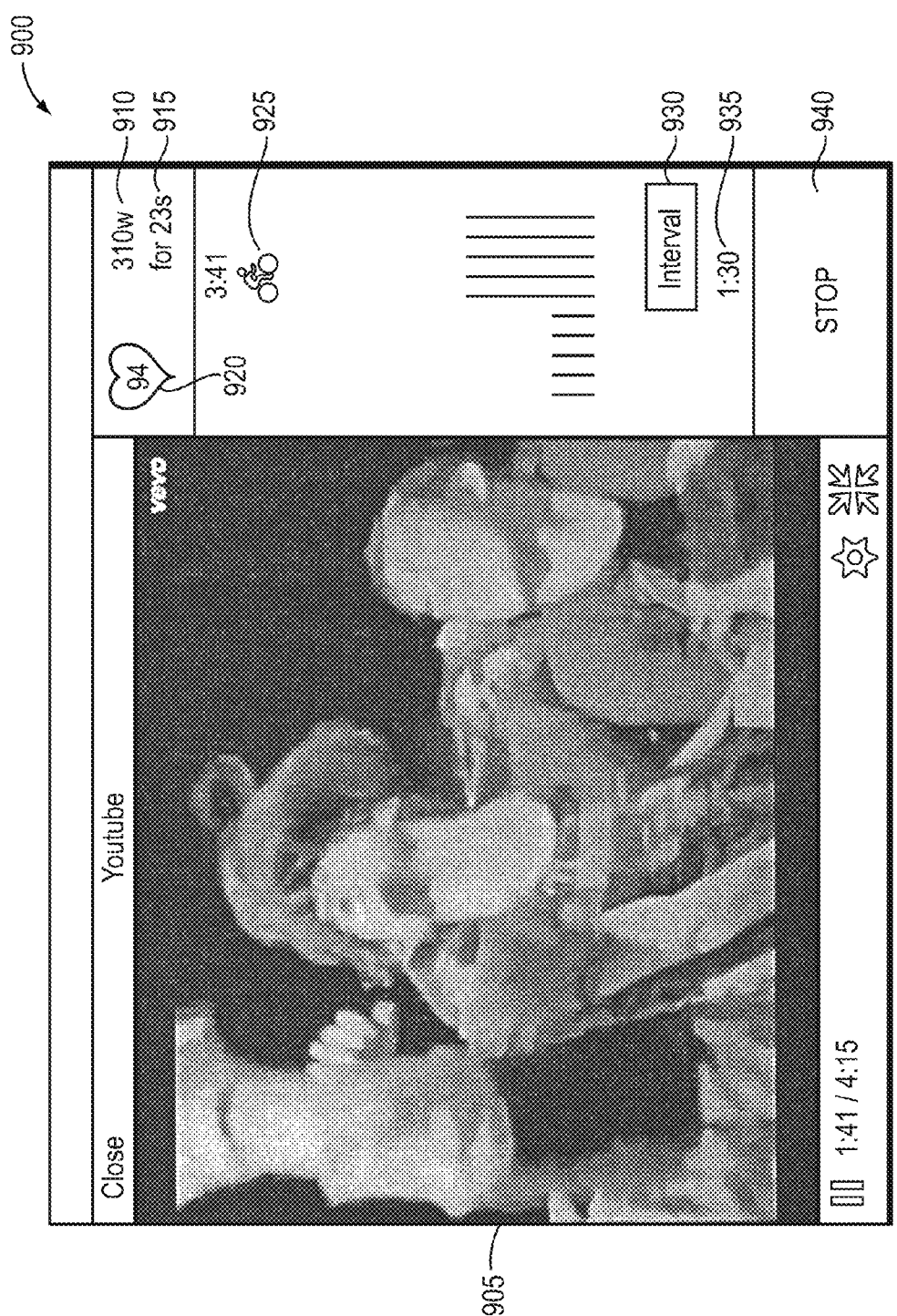
FIG. 9 is an exemplary screenshot illustrating a window displayed during a fitness test in accordance with an illustrative embodiment of the present invention.

FIG. 9 is an exemplary screenshot illustrating a fitness testing window 900 in accordance with an illustrative embodiment of the present invention. The window 900 illustratively includes an entertainment section 905, energy indicator 910, time remaining field 915, heart rate indicate 920, activity indicator 925, workout intensity indicator 930, time indicator 935 and a stop button 940. Illustratively, the entertainment section 905 may display video for entertaining a user during a fitness session. For example, the entertainment section 905 may display YouTube videos, streaming videos from, for example, Netflix or other online streaming services, or the like. In alternative embodiments, entertainment section 905 may not be present. In further alternative embodiments, the fitness testing computer 300 may provide audio entertainment, for example, by streaming music or providing music playback functionality. As such, the description of the entertainment section 905 providing audiovisual capability should be taken as exemplary only. The energy indicator 910 indicates the desired amount of work the user should be expending during a particular interval. In the displayed example of FIG. 9, the user should be exerting 310 watts. The related time remaining field 915 indicates that the time remaining in a particular interval. When read in conjunction with the energy indicator 910, a user may determine how much exertion and for how long remains for a particular interval. The heart rate indicator 920 indicates the user's current heart rate. Illustratively, the user's heart rate is obtained from heart rate monitor 165. The workout intensity indicator and time indicator 930, 935 indicate or provide a visual indication of the intensity that the user should be exercising as well as the duration of a particular interval during the exercise session.

The stop button 940 is illustratively a touch screen button that a user may activate to indicate his or her desire to stop section. This may result of the user becoming fact he were otherwise desiring to exit the session. Illustratively, depression of the stop button 940 will cause the fitness testing application to 300 to exit the current fitness session.

Figure 10:
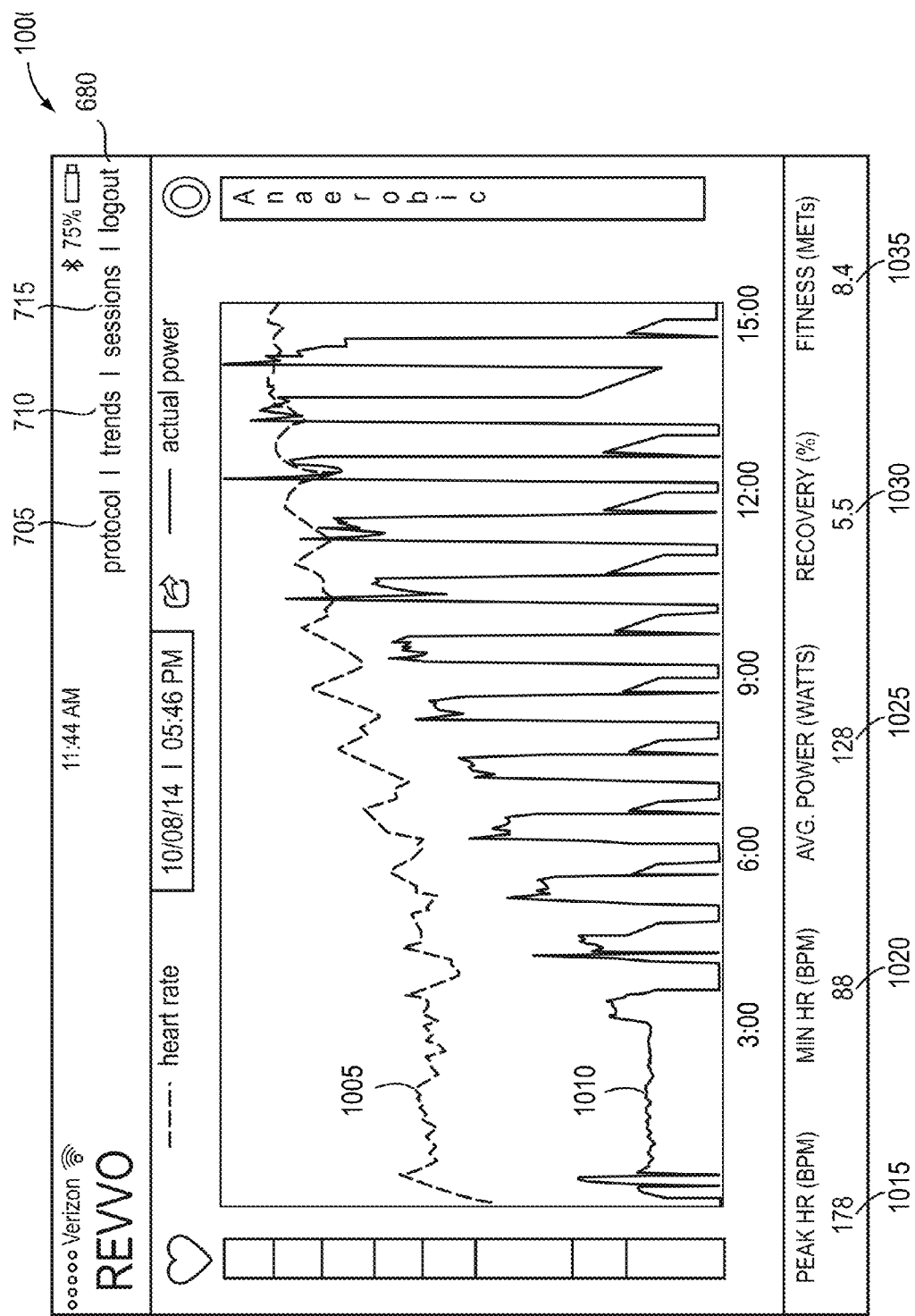
FIG. 10 is an exemplary screenshot illustrating a collected data display window in accordance with an illustrative embodiment of the present invention.

FIG. 10 is an exemplary screenshot illustrating a heart rate monitoring window 1000 in accordance with an illustrative embodiment of the present invention. Exemplary window 1000 provides a grasp of a heart rate 100 size and power worked 1010 during the various fitness sessions. Window 1000 also identifies a peak heart rate field 1015, a minimum heart rate field 1020, and average power field 1025, a recovery field 1030 and a fitness field 1035. Illustratively, the heart rate graph 1005 and actual power graph 1010 are shown along a time axis to enable user or administrator to view the relationship between heart rate and power worked by the user. The various display fields are utilized to display collected data during the fitness session.

Figure 11:
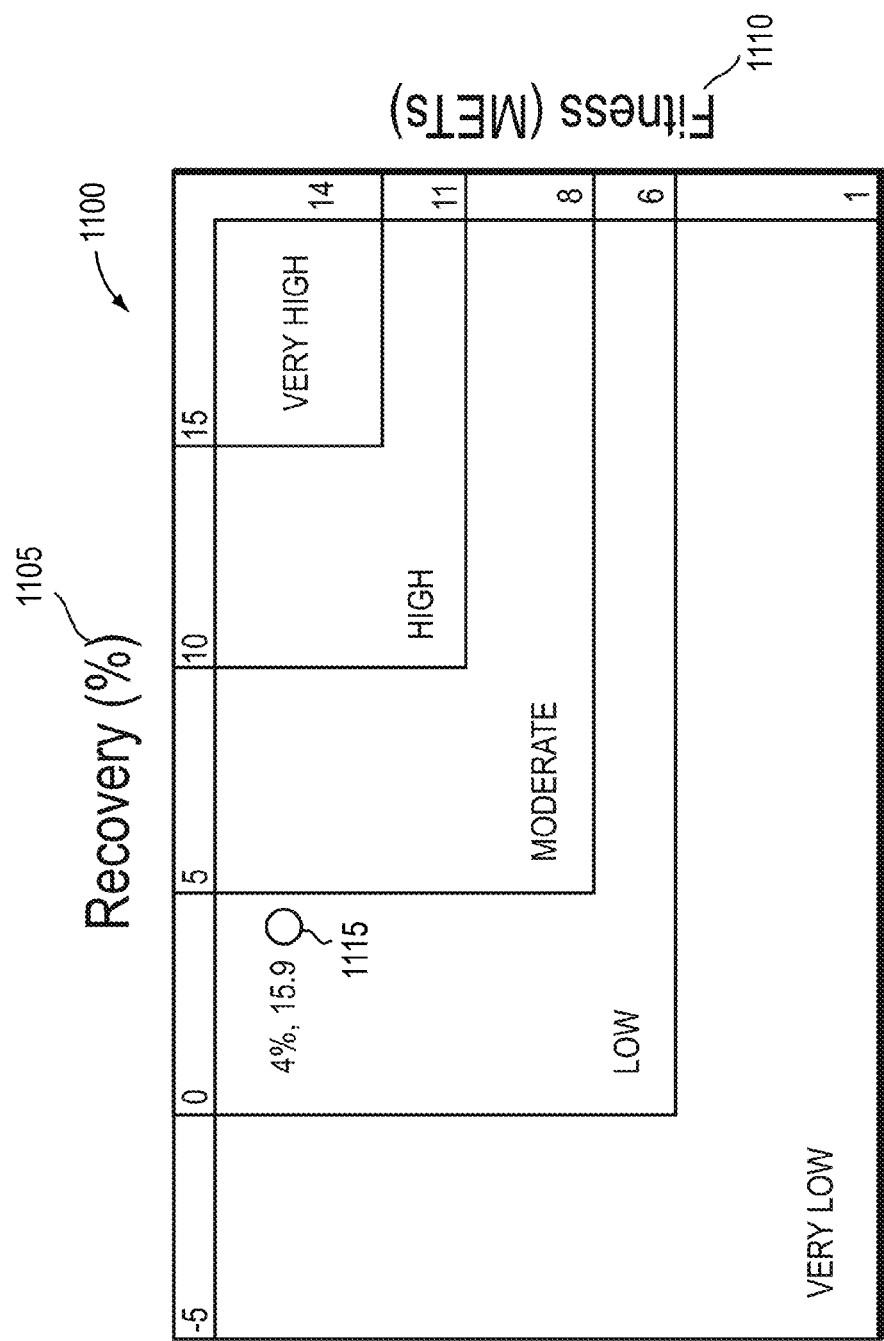
FIG. 11 is an exemplary screenshot illustrating a fitness and recovery results window in accordance with an illustrative embodiment of the present invention.

FIG. 11 is an exemplary screenshot illustrating a recovery window 1100 in accordance with an illustrative embodiment of the present invention. The recovery window 1100 displays a recovery percentage axis 1105 and a fitness level axis 1110. Illustratively, the fitness level is measured in METs. An exemplary data 0.1115 indicates that recovery is 4% while fitness is 15.9 METs. In accordance with an illustrative embodiment of the present invention, the fitness testing application 300 calculates appropriate values to be displayed to a user or administrator from the collected physiological data during a fitness session.

FIG. 12 is a screen shot illustrating an exemplary anaerobic threshold window 1200 in accordance with an illustrative embodiment of the present invention. Illustrative window 1200 computes anaerobic threshold ends displayed by the fitness testing application there illustratively, a maximum as was anaerobic threshold levels are displayed for power 1205, Mets 1210, VO2 1215 as well as road biking speed 1220. In accordance with an illustrative embodiment of the present invention, the power is displayed in Watts. And the road biking speed is converted from the other metrics to provide a user friendly value. Thus in the exemplary window displayed 1200, the anaerobic threshold is at 170 W, 9.9 METs and 35 V02 which equates to a 12.5 mph Road biking speed. During the fitness session in which this data was collected, the user reached a maximum of 275 watts and road biking speed of 16.6 mph. In accordance with the illustrative embodiments of the present invention, the fitness testing application 300 collect C various physiological data factors from a user during a fitness session to calculate the anaerobic threshold and then display it to the user or administrator.

FIG. 13 is a screenshot of an exemplary window 1300 in accordance with an illustrative embodiment of the present invention. Exemplary window 1300 displays example calculations that utilized to estimate the fitness of a particular user.

Figure 14:
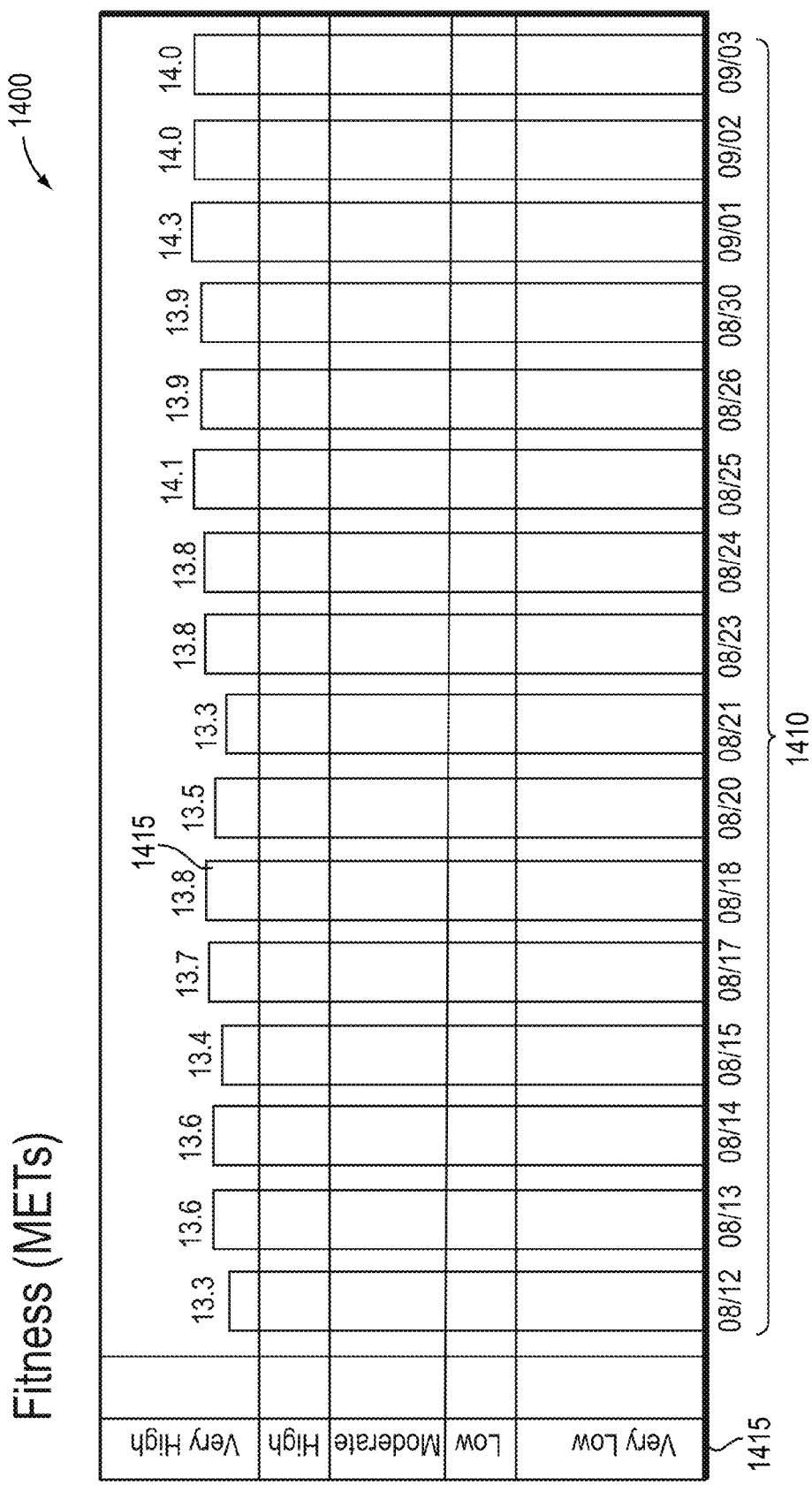
FIG. 14 is an exemplary screenshot illustrating a calculated fitness window in accordance with an illustrative embodiment of the present invention.

FIG. 14 is an exemplary screenshot illustrating a fitness graph window 1400 records with an illustrative embodiment of the present invention. The exemplary window 1400 includes an y-axis of fitness measured in Mets 1405 and y axis of dates 1410. For each date in which the data is collected, the calculated fitness is displayed. For example, exemplary entry for August 18 1415 shows a fitness in METs of 13.8. Illustratively, a user and/or administrator may scroll left and right back the users improvement or changes in their fitness level.

Figure 15A:
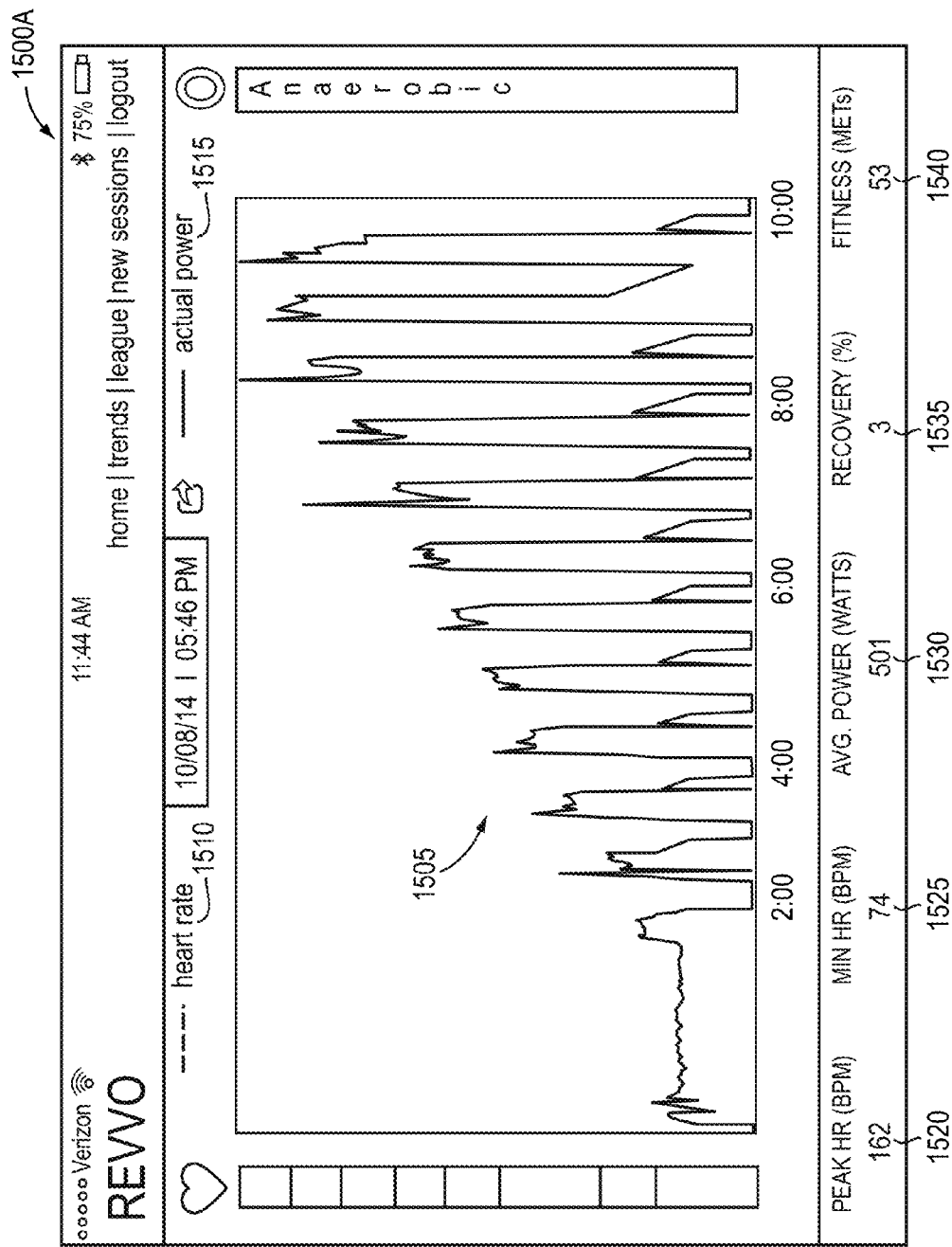
FIG. 15A is an exemplary screenshot illustrating an adaptive interval training window in accordance with an illustrative embodiment of the present invention.

FIG. 15A is a screenshot of an exemplary adaptive training window 1500 in accordance with an illustrative embodiment of the present invention. The window 1500 provides a graph of heart rate 1005 and power 1010 shown across a time period of multiple intervals during adaptive interval training. Collectively, window 1500 illustrates when the heart rate is entered in anaerobic level and further provides graphic information relating to recovery times.

Figure 15B:
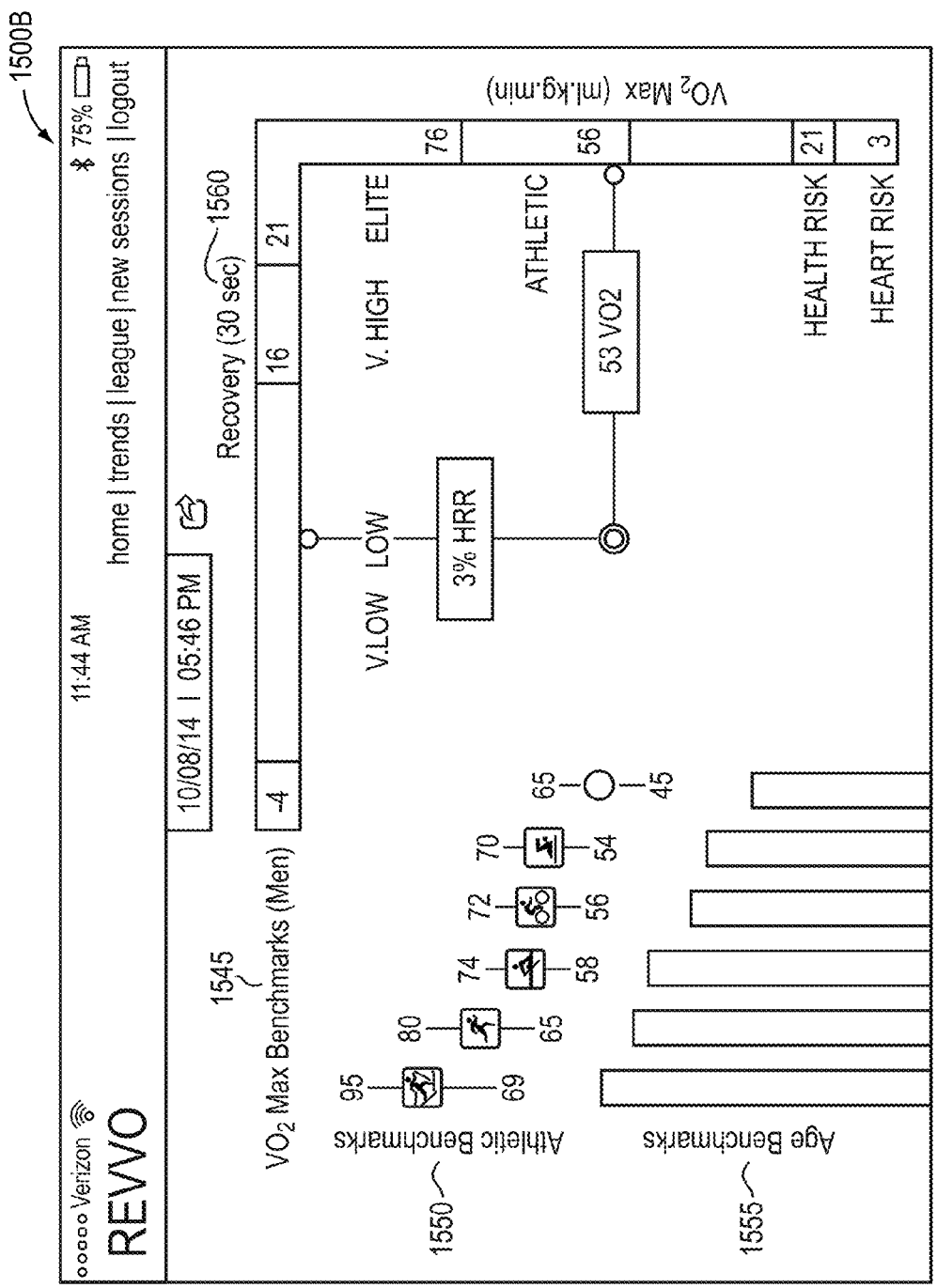
FIG. 15B is an exemplary screenshot illustrating an VO2Max benchmarks window in accordance with an illustrative embodiment of the present invention.

FIG. 15B is an exemplary screenshot illustrating an VO2Max benchmarks window in accordance with an illustrative embodiment of the present invention.

Figure 16:
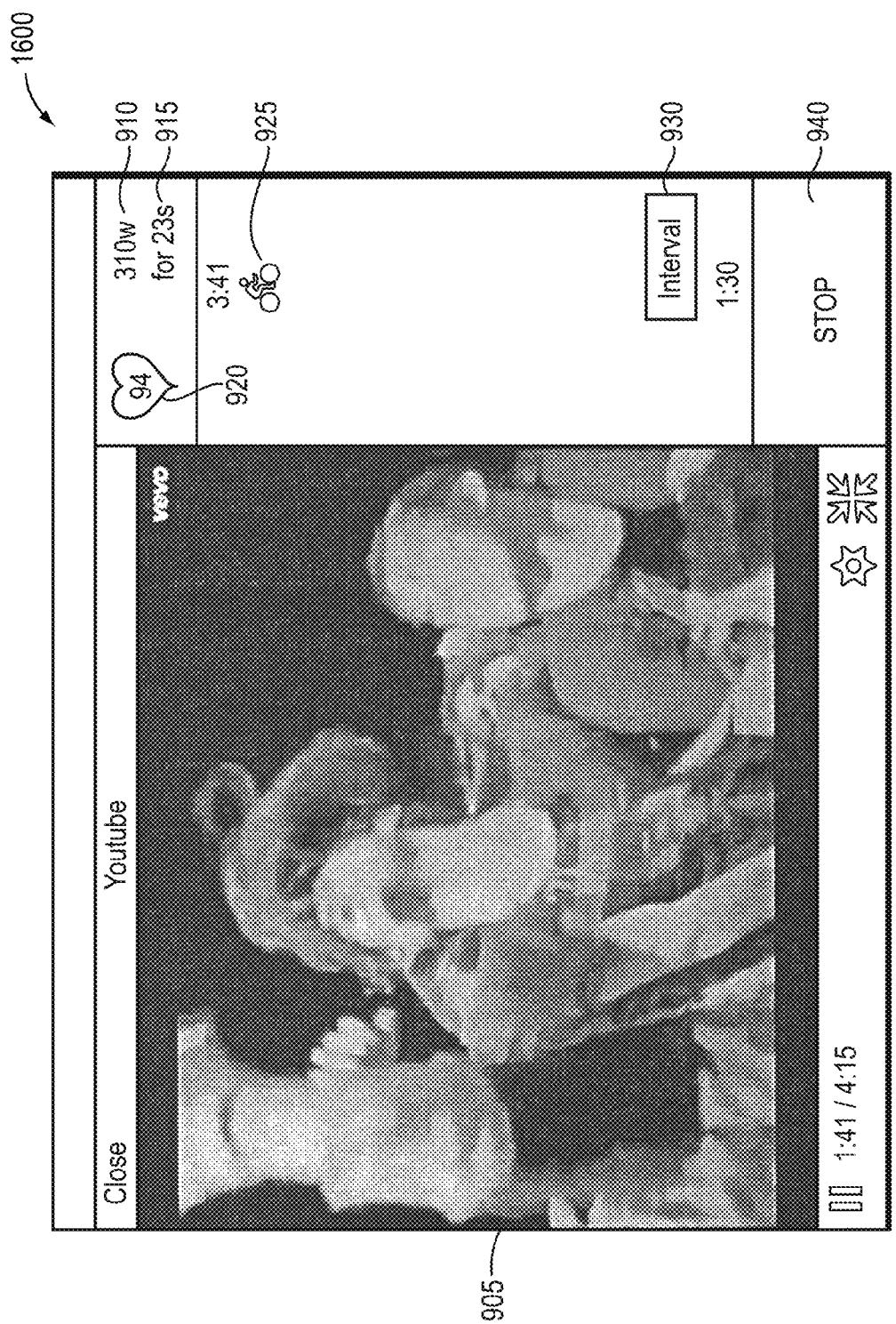
FIG. 16 is an exemplary screenshot illustrating a workout window in accordance with an illustrative embodiment of the present invention.

FIG. 16 is an exemplary screenshot of a training window 1600 in accordance with an illustrative embodiment of the present invention. Window 1600 is displayed during a training session to enable a user to track their progress during the session.

Figure 17:
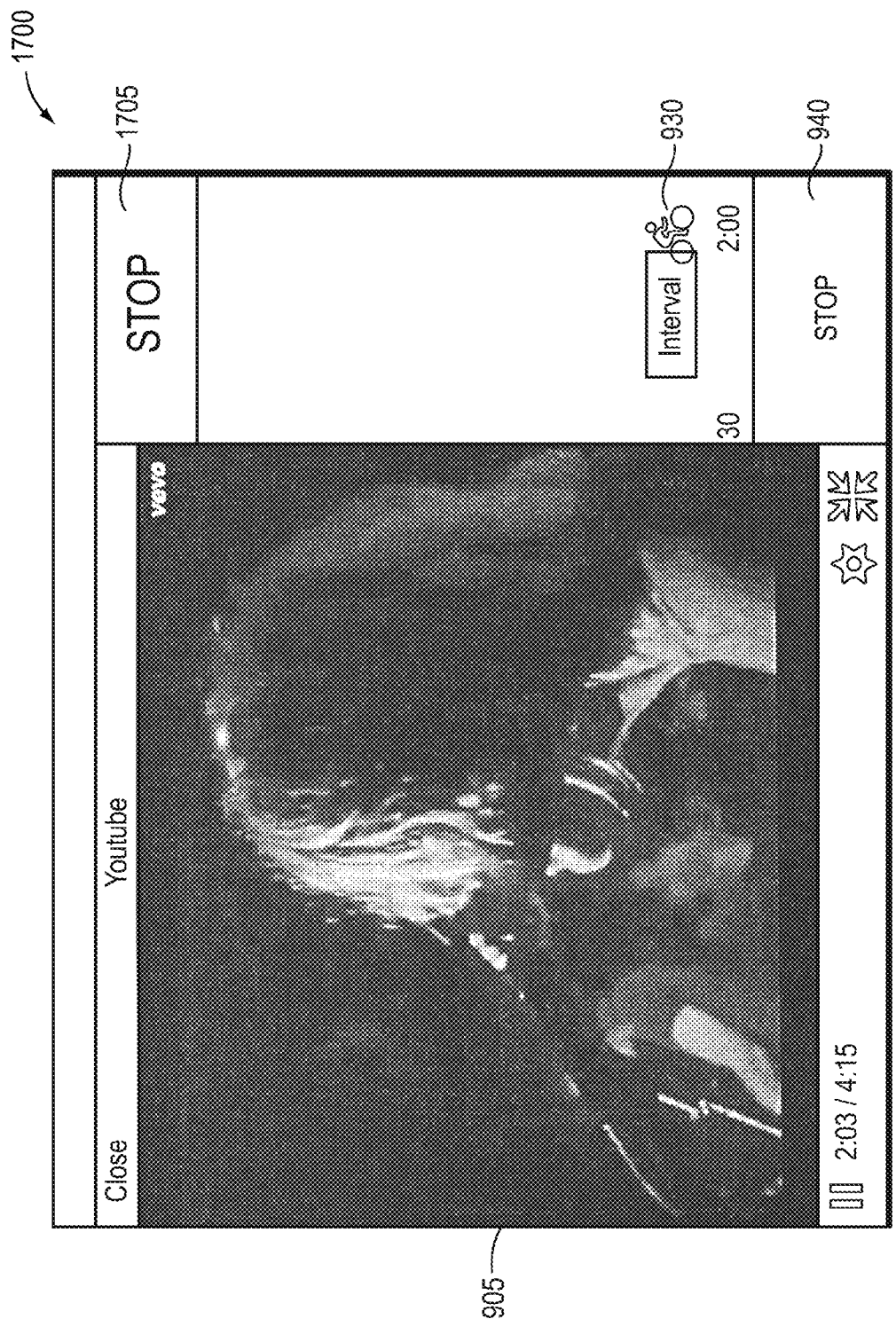
FIG. 17 is an exemplary screenshot illustrating a completion window in accordance with an illustrative embodiment of the present invention.

FIG. 17 is a screenshot illustrating an illustrative completion window 1700 in accordance with an illustrative embodiment of the present invention. The window 1700 includes entertainment section 905, stop indicator 1705, interval timing indicator 930 and stop button 940. Illustratively, when an interval has completed, a stop indicator 1705 is indicated or displayed to alert the user that they should reduce energy output and begin a rest period. Illustratively, the stop indicator provides a visual indicator to a user that they need to begin a resting interval. Should the entire fitness session be completed, the stop indicator 1705 may indicate that there is not a further work interval to be scheduled to occur.

Figure 18:
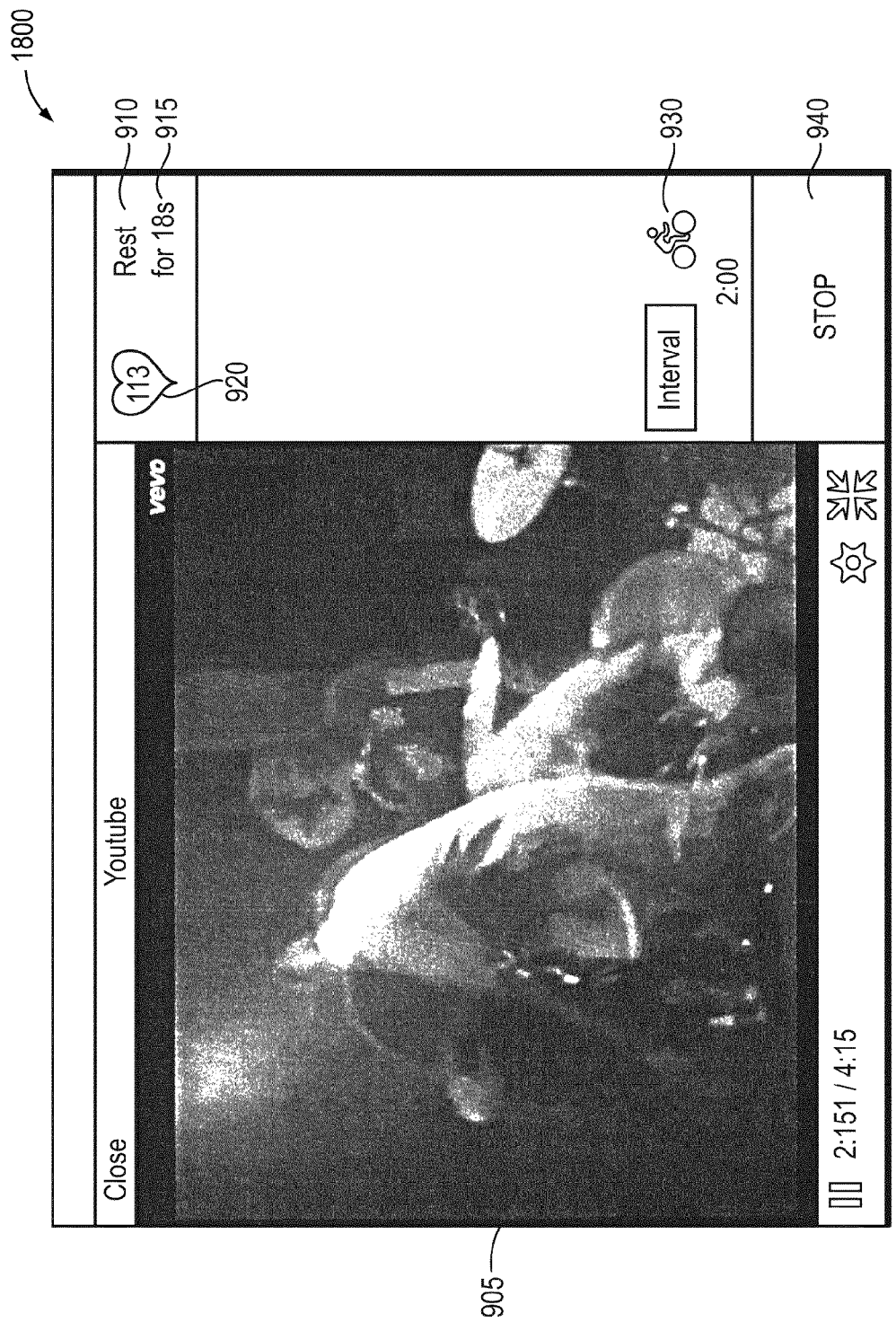
FIG. 18 is an exemplary screenshot illustrating a rest window in accordance with an illustrative embodiment of the present invention.

FIG. 18 is a screenshot illustrating an exemplary heart rate recovery window 1800 in accordance with an illustrative embodiment of the present invention. The window 1800 illustrative includes an entertainment section 905, a activity indicator 910, a time remaining indicator 915, heart rate indicator 920 interval indicator 930 and stop button 940. As can be seen in exemplary window 1800, the activity indicator 910, 915 is indicating that user should be resting for an additional 18 seconds and that the user's heart rate is currently 113 bpm. Exemplary window 1800 may be displayed during set rest intervals to provide visual feedback to the user as to the length or duration of their rest. That is, exemplary window 1800 may be utilized to indicate to a user that they should be resting and not exercising at a at load workout level.

Figure 19:
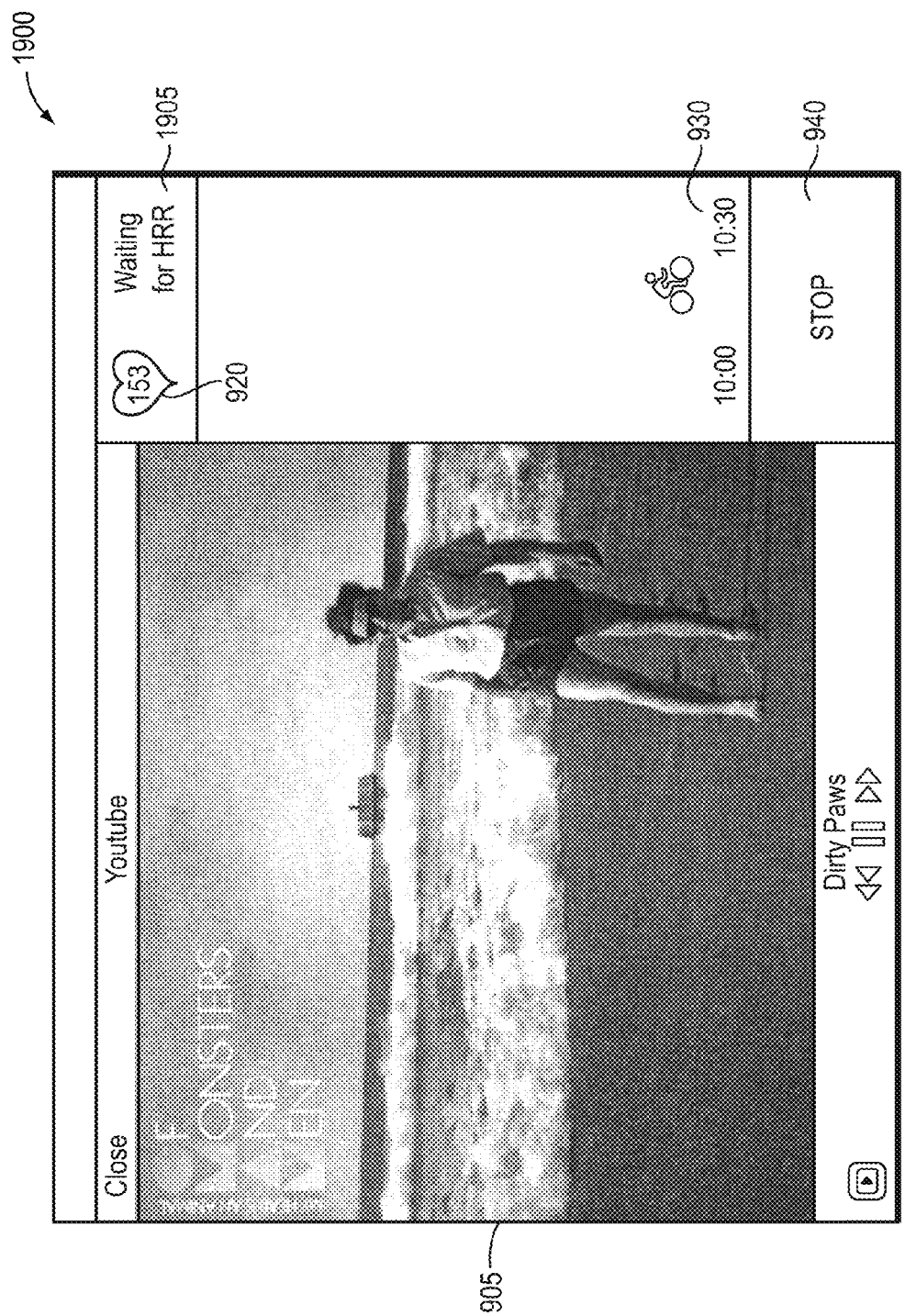
FIG. 19 is an exemplary screenshot illustrating a heart rate recovery window in accordance with an illustrative embodiment of the present invention.

FIG. 19 is an exemplary screenshot illustrating a heart rate waiting window 1900 in accordance with an illustrative embodiment of the present invention. The window comprises an entertainment section 905, a heart rate waiting indicator 1905, heart rate indicator 920, status indicator 930 and stop button 940. In accordance with an illustrative embodiment of the present invention, should a user's heart rate not meet a predefined recovery threshold, window 1900 will be displayed to the user indicating that the next interval is not going to begin until the user's heart rate has met a predefined threshold. In such case, the waiting indicator 1905 will be displayed in the space of the normal activity indicator. By displaying exemplary waiting indicator 1905, fitness testing application may ensure that a user has appropriately recovered prior to beginning the next interval. Further, in accordance with an illustrative embodiment of the present invention, the fitness testing application may also record the length of time required for a user's heart rate to recover to a predefined threshold. Changes in recovery times may be utilized as a metric in determining changes to a user's fitness level in accordance with the illustrative embodiments of the present invention.

Figure 20:
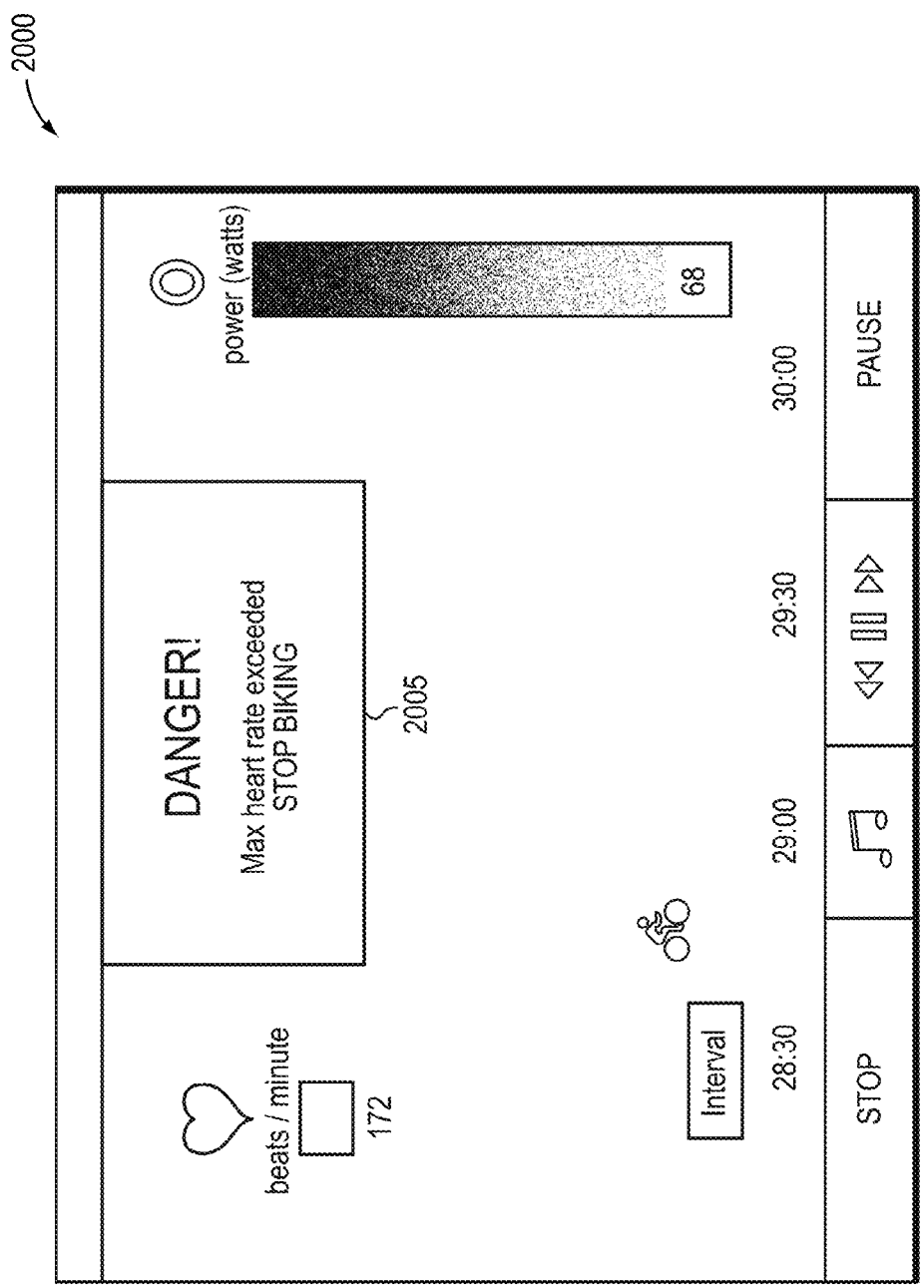
FIG. 20 is an exemplary screenshot illustrating an alert window in accordance with an illustrative embodiment of the present invention.

FIG. 20 is an exemplary screenshot illustrating a warning window 200 in accordance with an illustrative embodiment of the present invention. The warning window 2000 illustratively comprises a warning indicator 2005. It should be noted that the warning indicator 2005 may be displayed in any of the other windows described herein. In accordance with an illustrative embodiment of the present invention, should the fitness testing application detect that a user's heart rate has exceeded a preset maximum heart rate, then the warning indicator 2005 is displayed to inform the user to cease physical activity to enable their heart rate to recover. The warning indicator 2005 may also be coupled to other safety indicators. For example, an audio alert may be sounded body fitness testing application to provide a warning that the user should cease exercising. Further, in alternative embodiments, the fitness testing application may cause the bike trainer 160 to reduce providing resistance to reduce the workload being performed by the user. As such, the description of a warning indicator 2005 being displayed should be taken as exemplary only.

The fitness testing application leads the user through the session and collects data in step 440. The fitness testing application stores the collected data in step 445. Examples of data that is collected by the fitness testing application include, for example, heart rate, amount work, rest intervals, heart rate recovery times, etc.

As indicated above, the fitness testing application data may be stored within storage of the testing computer in accordance with an illustrative embodiment of the present invention. In alternative embodiments, the data may be stored in a cloud-based storage environment. As such, the description of data being stored either locally on the fitness testing computer or any cloud-based storage environment should be taken as exemplary only.

In addition to collecting the data, the fitness testing application's various metrics in step 450. The application may display the computed metrics in step 455. The procedure 400 then completes in step 460.

Fitness Testing Technique:

Most fitness tests conducted today (particularly those done with the intent to estimate the test subject's cardio-respiratory fitness ($VO_2Max$ or METs) typically require the participant to ramp up their exercise intensity after a set time period and continue doing so until the user reaches exhaustion (or a pre-set HR threshold). Various measurements taken during this process allow an estimation of the user's cardio-respiratory fitness.

The illustrative fitness testing approach described herein is unique in using a novel intermittent 30-second ramp protocol to assess the user's fitness. After an initial warm-up is completed (at a pre-determined, personalized intensity & duration) the user then works out at a higher intensity for a set period of time (e.g., bike at 70 watts for 30 seconds). At the end of that period the user stops activity completely and rests for a predetermined period (e.g., 30 seconds) and then resumes activity but now at a higher intensity target (e.g., 100 watts for 30 seconds) and then rests again at the completion of this activity. This process is repeated with ever increasing intensity until voluntary exhaustion is reached or a pre-determined threshold is reached (e.g., 90% of estimated HR max). The user's heart rate and energy expenditure (e.g., power in watts)—as well as potentially other metrics such as $VO_2/VCO_2$ ratio, galvanic skin response etc. are measured throughout the fitness test.

On completion the average power for each episode of activity (interval) is calculated (either for the entire interval or for a sub-set of the interval after stable state is reached). The heart rate response for each interval of activity is also computed. The Peak Exercise Capacity of the individual (Estimated Peak Power) is then calculated basis an estimate of the stable state activity (expressed for example in watts) and corresponding heart rate response:

EPP=Stable State Activity (Watts)/Heart Rate Response (bpm)*Max HR where Max HR for an individual is computed using a previously published/validated approach (such as Max HR=220-age). In alternative embodiments, the calculation of Max HR may vary depending on whether a sub-maximum test or a maximum test is being performed. In a maximum test, the heart rate response for the highest estimated EPP value is used as the Max HR. For a sub-maximum test, the Max HR may be determined using one of the previously published/validated approaches as described above.

Heart Rate Response can be estimated in a number of different ways—peak HR at the cessation of activity, peak heart rate following the cessation of activity, average heart rate for the entire interval, HR change during the interval and so on. The exact method could change over time to improve the accuracy of the estimation process and could be different for different types of individuals.

The average power values tend to increase as the intensity of the interval increases and get closer to the individual's Peak Exercise Capacity. The highest estimated average power value is considered as the Peak Exercise Capacity of the individual. While there is a well established relationship between oxygen intake and energy expenditure (Joules or watts), not all energy expenditure is directly due to oxygen intake. Some of it is 'anaerobic' i.e. does not require oxygen intake and is through breakdown of glycogen previously stored in muscles. The contribution of glycogen to energy expenditure increases as exercise intensity crosses the anaerobic threshold. Therefore the key challenge is to determine what proportion of energy expenditure is due to oxygen intake and what proportion is anaerobic. Once such a determination is made, VO2Max can be estimated by converting the aerobic component of peak energy expenditure from say watts or Joules to VO2 units based on well established equations.

To determine the aerobic-anaerobic contribution to energy expenditure, we first determine the anaerobic (lactate) threshold (using methods described below). In simple terms, above the anaerobic threshold we should expect VO2/energy expenditure ratio to be lower than below the anaerobic threshold. To estimate this, we treat heart rate response as a surrogate for VO2 response. As expected above the anaerobic (lactate) threshold heart rate response/energy expenditure ratio is lower than below the anaerobic threshold. We then compute the aerobic component of power output above the anaerobic (lactate) threshold by using heart rate response below the threshold as the baseline value—this is the denominator (this could be for example an average of values below the anaerobic threshold or the max value). And using a similar measure of heart rate response for the interval with highest achieved power as the numerator. This ratio (of heart rate response) tells us the contribution of aerobic metabolism to the peak power output and helps us separate the aerobic component of that power output so we can estimate peak oxygen uptake based on equations described above.

In this context heart rate response could be the actual HR either at start, at the end or the average heart rate during the interval or it could be the difference in heart rate between the start and end or even the rate of change/slope of heart rate between the start and end of the interval or any other suitable marker of time that best represents the corresponding period of energy expenditure VO2Max is then estimated from the Aerobic Component of Peak Exercise Capacity basis previously published ACSM equations (e.g., (6.12*EPP+7)*1.8/(Weight(lbs)*0.453592)). This can also then be converted to METs from the following ratio 1 MET=3.5 $VO_2$.

The exact parameters of the fitness test-power target for the warm-up, power target for each subsequent interval, rate at which the power target increments/ramps us between intervals are all personalized for each individual based on an expected fitness value for that individual. This makes the entire fitness test more do-able for the individual and increases the possibility that we obtain an accurate estimate of their cardio-respiratory fitness. And by enabling the user to get closer to their maximum cycling capacity (due to the intermittent ramp protocol) this method, in conjunction with a method to determine the aerobic component of peak power, is able to get a better estimate of their $VO_2$Max in comparison to traditional exercise testing protocols.

This expected fitness value could be calculated based on known age/gender averages or pre-existing information collected from other study participants or by using published algorithms (e.g. NASA method) that can estimate cardio-respiratory fitness from easily measured data about the individual (e.g. height, weight, age, gender, waist girth, fat mass and so on).

HR Recovery Measurement

Traditionally heart rate recovery has been measured as a single point measure of the change in heart rate post the completion of a maximal exercise test. There have been varying time frames used to calculate the change—30 seconds to 3 minutes being the most common.

However relying on just a single point of data to measure heart rate recovery could make it more volatile, less robust and perhaps not fully representative of the person's physiology. Also the measurement is subject to inter-person differences in peak exercise intensity, particularly in sub-maximal tests where users rarely achieve their peak capacity during the fitness test.

The illustrative fitness protocol described above uses an intermittent ramp protocol—thereby creating the opportunity to measure heart rate recovery multiple times during the course of a fitness test. As described above, users cycle at a specific intensity for a set amount of time (e.g., 30 seconds) followed by a period of rest for a set amount of time (e.g., 30 seconds). Heart rate is measured continuously—the difference between the heart rate achieved prior to the cessation of activity at the end of each bout of cycling and the heart rate 30 seconds after the cessation of activity at the end of each bout is averaged across all valid intervals to calculate an estimate of heart rate recovery for that user.

The resulting estimate relies on multiple data inputs (typically 8 or more) and is therefore potentially more robust than traditional single-point heart rate recovery measurements. And since users' recovery is measured at different intensities, it reduces bias that could occur from measuring at just a single intensity.

The resulting estimate of heart rate recovery is also a good predictor of the user's cardio-metabolic health, with low heart rate recovery correlating strongly with poor cardio-metabolic health indicators such as hypertension, hyperglycemia, hyperlipidemia, anaemia etc. Low heart rate recovery as measured above also tends to correlate with excessive body weight.

Anaerobic (Lactate) Threshold Measurement

The Anaerobic Threshold is commonly measured by either blood lactate (lactate threshold) or ventilatory gases (ventilatory threshold). However both these methods have shortcoming when it comes to application in daily practice. The lactate threshold requires drawing of blood to measure lactate levels while the subject participates in a ramped exercise protocol. The ventilatory threshold requires that the user wear a gas mask that captures expired gases and uses the $VCO_2$ to $VO_2$ ratio to determine if the subjects ventilatory threshold has been crossed. Due to this both methods have remained in labs and not transitioned to daily or home use.

Other more simpler approaches have been tried—the Conconi method is one approach that compares the heart rate to energy expenditure during a ramped exercise protocol—the point at which the heart rate/EE relationship goes from being linear to logarithmic is considered the anaerobic threshold. This method has relied on the insight that the body uses less oxygen when engaged in anaerobic activity, and therefore cardiac output does not rise in proportion to energy expenditure when the subject transitions to predominantly using the anaerobic metabolism. While this is relatively easy to implement it does not seem to consistently work with multiple studies often drawing widely divergent conclusions.

The illustrative embodiment of the present inventions takes a different approach to comparing heart rate data to energy expenditure to estimate the anaerobic threshold. In simple terms, the illustrative method relies on the level of heart rate recovery post the completion of a bout of cycling to determine if the energy expenditure during the cycling bout (measured e.g., in watts) was above or below the anaerobic threshold. The subject follows the intermittent ramp protocol described above. Heart Rate Recovery is calculated after each bout of cycling as described above. It is observed that the rate of heart rate recovery declines as the intensity of the intervals increases—but this shift is non-linear. i.e. at a particular threshold intensity the level of heart rate recovery is markedly lower than earlier—this intensity is determined as the upper bound of the anaerobic threshold. The intensity just below is considered as the lower bound of the anaerobic threshold with the actual threshold lying somewhere in between these two bounds. In general, the level of heart rate recovery (i.e. 1 minus the difference between the heart rate on cessation of the interval versus heart rate 30 seconds later as a function of the heart rate on cessation) tends to drop below 10% as the subject crosses the anaerobic threshold during the abovementioned fitness protocol. In other embodiments, other types of heart rate patterns are measured for each bout of cycling and can be similarly used to determine the anaerobic threshold. For example this could be the average heart rate corresponding to the bout of cycling or the rate of change of heart rate from the commencement of the cycling bout to it conclusion or the absolute or percentage difference in heart rate between the start and end of the bout or the amplitude of the heart rate response curve to each level of energy expenditure It can be visually observed that the amplitude of heart rate response and the trend line varies as the energy demand increases. At lower levels of energy expenditure, heart rate response is moderate and thre trendline is flat reflecting the use of fat as the primary fuel. As energy demand increases, the body switches increasingly to carbohydrates burnt for energy by using oxygen and that results in a higher 'ventilatory' demand that is reflected in a higher amplitude and a fairly proportional rise in the heart rate response curve. At even higher levels of energy demand, muscles start to utilize stored glycogen 'anaerobically' to support the higher intensity of demand and the heart rate response curve flattens and the amplitude declines. And the anaerobic threshold could be determine by comparing the values obtained on the chosen metric across different bouts for example it could be the power output corresponding to the average value, or the median value or the 2nd co-efficient of a 2nd degree polynomial or perhaps the point at which there is the greatest change in the chosen heart rate response metric when comparing values across different bouts. This is made possible by the intermittent nature of the cycling bouts, providing greater opportunity for distinctive heart rate patterns to be detected that helps in making a more accurate determination.

In simple terms the aerobic process relies on muscle utilizing oxygen to metabolize glucose in the bloodstream to create ATP, the core fuel. As muscle activity increases, cardiac output increases proportionally to support the activity—both the volume of blood (stroke volume) and the frequency of heart beats. However at some point the body is unable to increase the rate at which it metabolizes glucose in the blood and starts supplementing with stored glycogen stored in the muscular system—which can be metabolized without utilizing oxygen. This is called anaerobic metabolism. Cardiac output no longer needs to increase in proportion to increasing activity. However, on cessation of activity, cardiac output stays elevated to replenish lost glucose stores, slowing down the recovery process.

In an alternative embodiment, we could use the ratio of heart rate response to energy expenditure to determine the anaerobic threshold as a surrogate indicator of oxygen uptake (VO2) in response to energy expenditure. Initially VO2/heart rate response is muted as the body primarily relies on fat as fuel source. As exercise intensity, energy expenditure rises the body starts to rely more on carbohydrates—resulting in higher HRR/energy expenditure ratio. At some point this ratio peaks—this would be the Aerobic Threshold and starts to decline as the body starts to rely on greater proportion of stored glycogen and lactate (as a by-product) starts to buffer in the system. This point of transition could be determined by picking the HRR/energy expenditure ratio or setting limits for the absolute heart rate response values, by looking at the point of greatest transition.

In addition, this method is also able to differentiate between people with insulin resistance (i.e. type 2 diabetes) and those with poor cardio-metabolic health but without full blown diabetes. Essentially for those with insulin resistance/impaired glucose tolerance heart rate recovery is low at all intensities (even at very low levels) suggesting that the body is (i) unable to metabolize glucose effectively from the bloodstream & therefore is (ii) forced to rely on anaerobic mechanisms to a greater extent then healthier individuals.

Tracking Cardio Respiratory Fitness

Within a few days of starting an exercise program most users (especially those who have been sedentary) should start to see improvements in their fitness parameters—particularly cardio respiratory fitness but also heart rate recovery and their anaerobic threshold. Today the only way for a user to assess improvements in these fitness parameters is to repeat a fitness test after a few weeks—which can be expensive, time consuming and inconvenient and therefore is rarely done. As a result most people who start an exercise program don't see the most important improvements they are making in their fitness—which is a big reason why they tend to drop out.

Tracking changes in these metrics has a second equally important benefit—that is to change the exercise protocol so that it reflects the changes in the user's fitness. Most sedentary people should experience a very significant improvement in their fitness parameters with the right exercise program within a few weeks of starting. If the exercise protocol is not adapted to the changing fitness the user will effectively be exercising at a lower level of challenge than when they started & therefore will not likely continue to experience the same level of improvement as in the initial phase. Again a major reason why people drop out from their exercise programs.

Traditionally people have used other type of metrics to track their progress in an exercise program—for how long they were able to run, walk or bike, how much time they are active, steps taken or the average pace at which they completed the activity. However none of these metrics tell them if they are making meaningful improvements in the parameters described above—cardio respiratory fitness, heart rate recovery or the anaerobic threshold. Also importantly, none of these measures are proven to correlate as well with health metrics as cardio respiratory fitness and heart rate recovery.

At a very simple level it is possible to infer improvements in fitness by taking into account the relation between heart rate—energy expenditure. As the heart rate per unit of energy expenditure declines it indicates that the user's fitness is improving. However this does not provide a precise estimate of the magnitude of change. Secondly (& importantly) this is affected by the quantum and intensity of the energy expenditure. In general varying quantum of energy expenditure results in varying heart rate—energy expenditure relationship even without any change in the underlying fitness. Same goes for intensity—differing intensities of energy expenditure result in differing heart rate—energy expenditure relationships.

The novel method developed solves this problem by first developing a personalized algorithm for each individual based on their initial fitness test—relating their 'Estimated Peak Power' at different intensities to their highest Achieved Peak Power during the fitness assessment. The relationship between the intensity at which they cycled and the estimated peak power at that intensity (which is a function of their heart rate at that intensity—methods described above) is typically log-linear. Personalizing this i.e. fitting a unique curve for each user results in a better fit (approaching an R_square of 0.99) compared to aggregating across individuals (which results in R-square values of 0.70 or less). Once this relationship is estimated from the initial fitness assessment it becomes fairly straightforward to subsequently estimate changes in the user's fitness during a regular exercise session. The user's heart rate to energy expenditure relationship is either captured by aggregating data across the entire session or by sampling specific points during the session or through a combination of both methods. This is then inputted into the personalized algorithm to generate a new estimate of the user's peak power (EPP). The resulting estimate of Peak Power (watts) is then converted into $VO_2Max$ values and METs based on methods described above using standard ACSM equations.

By normalizing this resulting estimate against the original estimate generated in the fitness test it is possible to further improve the accuracy of the estimation process. In an alternative embodiment, this may also allow the algorithm to be adjusted for variation in equipment calibration and data capture between the equipment used for testing and that used for training. This is best done from data obtained in the first exercise session that immediately follows the fitness assessment. The resulting adjustment factor is applied to all subsequent measurements. And by repeating the fitness test at regular intervals (e.g. every 3 months) it is possible to further improve the accuracy of the estimation.

Tracking Heart Rate Recovery

Measuring ongoing improvements in heart rate recovery is also very valuable to the exerciser—as described earlier heart rate recovery levels are able to discriminate between those with poor cardio-metabolic health and the rest. Therefore improvements in heart rate recovery would indicate underlying improvements in the user's cardio-metabolic health.

Traditionally heart rate recovery has been measured from the time of cessation of peak energy expenditure during a maximal or sub-maximal test & therefore it has not been possible to track improvements in heart rate recovery without repeating a fitness test.

The illustrative technique for measuring heart rate recovery discussed above is based on average heart rate recovery across the entire intermittent ramped protocol based fitness test. At each intensity level, it is possible to determine an expected rate of heart rate recovery and then compare that to the actual heart rate recovery for the same intensity during a regular exercise session. The ratio between the two is then applied to the average heart rate recovery metric previously established from the fitness test to determine a new estimate for heart rate recovery.

The accuracy of this estimate can be further improved by (i) using multiple points of data to estimate the heart rate recovery during an exercise session rather than relying on a single point of data (ii) by adjusting for natural differences in the metrics between the initial fitness test and the first exercise session that immediately follows the test and using that adjustment factor on all subsequent sessions.

It is expected that this resulting metric would be a reliable estimate of improvements in cardio-metabolic health comparable to traditional measurements such as fasting plasma glucose, blood pressure or A1C thereby providing an effective measure of 'root cause' that underlies much of the cardio-metabolic conditions, thereby enabling the use of treatments and modification of exercise protocols that improves this measure of underlying cardio-metabolic health. Further, it is also expected that the metric correlates or otherwise predicts other factors affecting parasympathetic training, e.g., sleep, stress, over-training, illness, that may prevent a normal recovery.

Fitness Improvement Via Adaptive Interval Training

Today, exercise recommendations tend to be generic—people are told to do the things they like, complete 10,000 steps each day or spend 30 minutes exercising. Much of this activity tends to be continuous and aerobic, often at intensities that are relatively low. As a result its not a surprise that people don't see a quick benefit from exercising and tend to give up. In particularly focusing on increasing activity is not as effective to improve someone's health as increasing their fitness.

Recent studies in exercise science are showing quite clearly that high intensity interval training is approximately two times more effective than continuous exercise in improving a user's fitness. Interval training is also time efficient & therefore better able to fit into people's lifestyles. However high intensity training (which typically requires that user's workout above their max, potentially up to approximately 170% of their max, for a fixed period—say 30 seconds and then rest for a fixed period—repeated multiple times) is not viable for people who have been sedentary for a while and could even be potentially dangerous if applied by someone with existing cardio-metabolic health issues.

Therefore it was necessary to create an exercise protocol that provides the benefits of high intensity interval training but without the safety concerns—the proposed invention achieves that goal. The proposed novel exercise protocol (called 'Adaptive Interval Training') uses as input the user's cardio-respiratory fitness and anaerobic threshold measured through the initial fitness test. It then generates a personalized exercise plan for that user given constraints—say a certain period of time (e.g. 10 minutes). The exercise plan consists of a warm-up phase—duration and intensity. e.g. cycle for 30 watts for 90 seconds, followed by an interval (short bout of cycling for a fixed time at a particular intensity e.g. cycle for 320 watts for 30 seconds) and then recovery (cycle at low speeds or completely rest for a given period). The intensity of the warm-up period is determined as a function of the user's cardio-respiratory fitness (e.g. 10% of the user's fitness level), or an intensity at or just below the user's lactate/anaerobic threshold derived from the personalized heart-rate/work-rate relationship estimated during the initial fitness test).

The initial intensity for the interval is selected to target one of the fitness metrics measured through the test itself, such as the anaerobic threshold of the individual (measured via the initial fitness test) or the VO2Max, depending on the user's desired goals. For individuals where the anaerobic threshold could not be determined this could be a certain proportion of their overall cardio-respiratory fitness (say 50%). In some cases, the initial intensity could be set below the anaerobic threshold for the first few sessions and increased gradually to the anaerobic threshold after success in completing the session. The intensity could also be selected as a % of the target value to create variation in the exercise protocol—either a fixed % following a certain schema or a random % of the target value.

The length of the recovery period is the key variable that affects both the 'toughness' of the exercise session as well as the total number of intervals required to be completed (given a pre-set session time) or total session time given a pre-set # of intervals. Typically interval training programs set a specific time based recovery period (as either a fixed time period or a multiple of the interval time). Picking a fixed recovery period could make it too difficult for some and too easy for others depending on their level of fitness. Also our own research suggests that recovery needs change during the exercise session—for the first few intervals recovery is usually quite quick but tends to lengthen for subsequent intervals until the cardio-muscular system reaches a point where it starts to adapt to the demands & therefore the recovery tends to improve. Therefore there is need for an adaptive exercise protocol that enables users to naturally recover depending on their individual recovery patterns. The proposed invention tracks the user's heart rate and waits for it to drop below a pre-set threshold before guiding the user to start the next interval. The heart rate recovery threshold could be an absolute value or a percentage of the user's max heart rate or could be set at the heart rate corresponding to their lactate threshold as measured through the initial fitness test. This has an additional benefit in that it makes each interval of relatively equal impact on the body & therefore allows the system to provide a consistent dose of interval training in the session.

Based on the time it takes the user to recover its possible to change the intensity target for the subsequent interval so that the user gets to complete a given number of intervals within the set time constraint. For e.g. if recovery is faster than usual the intensity target for the next session can be increased & vice versa.

Also even without changing the interval intensity target the overall demand on the user would automatically adapt to their day-to-day variation in fitness—if recovery is slower than usual then the user would get fewer intervals in that session & vice versa. A second level of adaptation is between sessions—the exercise protocol for each session is adapted basis the outcomes of the previous sessions based on a number of factors: (i) changes in the heart rate recovery at that intensity (ii) changes in cardio-respiratory fitness (iii) actual intensity achieved versus target intensity (iv) max heart rate during the session. This helps keep the level of challenge appropriate to the user's changing fitness parameters.

So if the heart rate recovery improves for that individual such that it is now above the limit for the anaerobic threshold then the intensity for the next session is increased so that the user continues to workout just above the anaerobic threshold. Significant changes in cardio-respiratory fitness (for e.g. if the user has not exercise for a while and their fitness has declined) would also trigger a change in the intensity target. In fact this change in intensity can be implemented during the second half of a session itself based on measured changes in cardio-respiratory fitness during the first half of the session.

The average intensity the user completes during the session could also trigger a change in the exercise intensity target for the subsequent session—if the average intensity is significantly higher than the target intensity or vice versa that could trigger a corresponding increase or decrease for the subsequent session.

If the maximum heart rate during the session exceeds a set threshold that could (i) trigger an immediate call to stop activity if the user is currently midway through an interval (ii) trigger an automatic reduction in the resistance of the exercise bike so as to prevent the user from cycling vigorously (iii) trigger a reduction in the exercise target for subsequent intervals (iv) trigger a reduction in the exercise target for subsequent sessions.

Maintaining Blood Pressure & Blood Glucose Levels During an Exercise Session

One of the key discoveries is that there is a relationship between the blood glucose levels and heart rate during an exercise session—therefore by controlling the heart rate it is possible to regulate blood glucose during an exercise session so that it stays within safe limits. If the user is exercising predominantly below their anaerobic threshold then blood glucose levels during the exercise program are inversely related to the heart rate data. Essentially as blood glucose levels decline through utilization there is a temporary fall that triggers a higher frequency of heart beats that raises cardiac output to compensate for the decline. This continues until the blood glucose levels approach the point at which counter-regulatory forces are triggered releasing glucose from the liver into the blood stream thereby meeting the demand for fuel and resulting in a decline in the heart rate.

When the user is primarily exercising above the anaerobic threshold blood glucose levels are positively correlated with heart rate—therefore as the heart rate increase, BG levels also increase. This is a reflection of the fact that when exercising above the anaerobic threshold the body uses glucose stored in the muscle, part of which gets released into the blood stream.

Therefore, by knowing whether the user is working above or below the anaerobic threshold and then controlling the intensity of the exercise to regulate the heart rate would automatically also regulate the blood glucose levels during the exercise program. So for example if the goal is to reduce the blood glucose level during the exercise program then the user can be guided to exercise below the anaerobic threshold and heart rate kept below a certain threshold to keep blood glucose low. Similarly if the goal is to prevent the user's blood glucose from dropping too low then the user is guided to exercise above the anaerobic threshold. In both situations making the recovery adaptive helps give time for the body to adapt to new fuel demands and therefore reduce the changes of triggering a very high or very low glucose excursion, making it safer for diabetes patients to exercise at intensity.

Its known that blood pressure during an exercise session is correlated with heart rate. The adaptive protocol keeps heart rate under control and thereby also prevents blood pressure from rising significantly.

Minimizing Risk of Hypoglycemia for Type 1 Diabetes Patients

Type 1 Diabetes is a condition in which the body stops producing insulin and therefore makes the patient completely dependent on insulin injections to modulate blood glucose. As a result Type 1's are very susceptible to blood glucose highs and lows—exercise is one of the factors that makes it difficult for them keep their blood glucose under control. Typically aerobic exercise tends to result in blood glucose lows and anaerobic exercise could result in blood glucose highs during the exercise session followed by a low 6-9 hours after the cessation of exercise. As a result most type is experience significant incidence of low blood pressure particularly during night time when it is difficult to detect or react to it.

The proposed exercise protocol reduces the risk of type 1 diabetes patients experience blood glucose highs or lows—either during the exercise session or post the session. The protocol sets the intensity of the intervals such that they alternate between above and below the anaerobic threshold. When the patients exercise just above the threshold blood glucose is released into the blood stream and is subsequently absorbed/utilized during the next interval which is set below the anaerobic threshold. As a result glucose homeostatis is maintained throughout the exercise session and does not result in unanticipated blood glucose highs or lows post the session.

The foregoing description has been directed to specific illustrative embodiments of the invention. It will be apparent, however, that other variations and modifications may be made to the described embodiments, the attainment of some or all of their advantages. Specifically, certain processes have been described as being performed in software and/or hardware. However, it should be noted that any of the processes maybe performed in software, hardware, firmware or a combination thereof. It should be noted that his various graphical user interface windows and screens have been described herein in relation to exemplary embodiments of the present invention. However, as will be appreciated by those skilled in the art, the layout, positioning, arrangement and/or design of various windows and screens may be varied considerably from those described here in while still retaining the desired goal and functionality in accordance with embodiments for illustrative embodiments of the present invention. As such, the various windows and screens described herein should be taken as exemplary only. Accordingly, this description is be taken only by way of example and not to otherwise limit the scope of the invention. Therefore, it is the object of the appended claims to cover all such variations and modifications as come within the true spirit and scope of the invention.

What is claimed is:

1. A system comprising:
an exercise apparatus operatively interconnected with a training device configurable to provide variable resistance to a user;
a fitness testing computer comprising a processor executing a fitness testing application, the fitness testing computer operatively interconnected with the training device and one or more physiological monitors, the one or more physiological monitors configured to provide physiological data to the fitness testing application;
wherein the fitness testing application is configured to execute an intermittent testing protocol comprising an interval fitness session for a user on the exercise apparatus, wherein the fitness testing application records the physiological data during the interval fitness session and is further configured to estimate the aerobic component of maximum energy expenditure measured through the intermittent testing protocol without using an oxygen mask.

2. The system of claim 1 wherein the exercise apparatus comprises a stationary bicycle.

3. The system of claim 1 wherein the fitness testing computer comprises a tablet computer.

4. The system of claim 1 wherein the one or more physiological monitors comprise a heart rate monitor.

5. The system of claim 1 wherein the fitness testing application is further configured to execute a training protocol comprising a training session and wherein the fitness testing application uses the results of the intermittent testing protocol to vary an intensity of the training session to regulate a heart rate of the user.

6. The system of claim 1 wherein the fitness testing application is further configured to execute a training protocol comprising a training session and wherein the fitness testing application uses the results of the intermittent testing protocol to vary an intensity of the training session to regulate blood glucose levels of the user.

7. The system of claim 1 wherein the fitness testing application is further configured to estimate heart rate recovery based on a plurality of heart rate measurements during execution of the intermittent testing protocol.

8. The system of claim 7 wherein the fitness testing application is further configured to estimate an anaerobic threshold based on heart rate response to different levels of energy expenditure during execution of the intermittent testing protocol.

9. The system of claim 8 wherein the intermittent testing protocol further comprises an initial fitness test.

10. The system of claim 9 wherein the initial fitness test establishes a baseline fitness level (VO2Max) and anaerobic threshold for the user.

11. The system of claim 8 wherein the fitness testing application is further configured to execute a training protocol comprising a training session and wherein the fitness testing application uses the results of the intermittent testing protocol to vary an intensity of the training session to keep a user working above the estimated anaerobic threshold or VO2Max.

12. The system of claim 8 wherein the fitness testing application is further configured to execute a training protocol comprising a training session and wherein the fitness testing application uses the results of the intermittent testing protocol to very an intensity of the training session to keep a user working below the estimated anaerobic threshold or VO2Max.

13. The system of claim 8 wherein the fitness testing application is further configured to execute a training protocol comprising a training session and wherein the fitness testing application tracks the estimated fitness metrics of the user during the training session by relying on a relationship between heart rate and energy expenditure established through the intermittent testing protocol.

14. The system of claim 8 wherein the fitness testing application is further configured to modify the intermittent testing protocol based on the physiological data recorded and estimated during the interval fitness session.

15. The system of claim 8 wherein the fitness testing application is further configured to modify the intermittent testing protocol based on the physiological data recorded and estimated during a previous interval fitness session.

16. The system of claim 1 wherein the intermittent testing protocol includes an intermittent ramp protocol with a predetermined time period and with varying resistance to the user.

17. The system of claim 1 wherein the fitness testing application is further configured to execute a training protocol comprising a training session and wherein the fitness testing application uses the results of the intermittent testing protocol to vary an intensity of the training session to regulate blood pressure levels of the user.

18. The system of claim 1 wherein the intermittent testing protocol further comprises one or more recovery periods and wherein the fitness testing application modifies the length of the one or more recovery periods based on a heart rate of the user.

19. A method for testing the fitness of a user comprising:
providing a fitness testing computer comprising a processor executing a fitness testing application, the fitness testing computer operatively interconnected with a training device configurable to provide variable resistance to a user, the training device operatively interconnected to an exercise apparatus, the fitness testing computer further operatively interconnected with one or more physiological monitors, the one or more physiological monitors configured to provide physiological data to the fitness testing application;
executing an intermittent testing protocol by the fitness testing application, the intermittent testing protocol comprising an interval fitness session for a user on the exercise apparatus,
wherein the intermittent testing protocol includes an intermittent ramp protocol with a predetermined time period and with varying resistance to the user; and
wherein the fitness testing application records the physiological data during the interval fitness session and is further configured to estimate the aerobic component of maximum energy expenditure measured through the intermittent testing protocol without using an oxygen mask.

* * * * *

UNITED STATES PATENT AND TRADEMARK OFFICE
CERTIFICATE OF CORRECTION

| | |
|---|---|
| PATENT NO. | : 9,737,761 B1 |
| APPLICATION NO. | : 14/926436 |
| DATED | : August 22, 2017 |
| INVENTOR(S) | : Govindarajan Sivaraj |

Page 1 of 1

It is certified that error appears in the above-identified patent and that said Letters Patent is hereby corrected as shown below:

In the Specification
Column 23, Line 4:
Delete "type is experience significant incidence of low blood pres-"
Insert --type 1's experience significant incidence of low blood pres- --

In the Claims
Claim 12, Column 24, Line 40:
Delete "protocol to very an intensity of the training session to keep"
Insert --protocol to vary an intensity of the training session to keep--

Signed and Sealed this
Twentieth Day of August, 2019

Andrei Iancu
*Director of the United States Patent and Trademark Office*